US007846435B1

(12) United States Patent
Matsumoto et al.

(10) Patent No.: US 7,846,435 B1
(45) Date of Patent: Dec. 7, 2010

(54) HUMANIZED ANTIBODIES THAT RECOGNIZE VEROTOXIN II AND CELL LINE PRODUCING SAME

(75) Inventors: Yoh-Ichi Matsumoto, Tokyo (JP); Atsuchi Imaizumi, Tokyo (JP); Tsuyoshi Kimura, Tokyo (JP); Tae Takeda, Tokyo (JP); Yoshifumi Takeda, legal representative, Tokyo (JP); Man Sung Co, Cupertino, CA (US); Maximiliano Vasquez, Palo Alto, CA (US)

(73) Assignees: Teijin Limited, Tokyo (JP); PDL Biopharma, Inc., Incline Village, NV (US)

( * ) Notice: Subject to any disclaimer, the term of this patent is extended or adjusted under 35 U.S.C. 154(b) by 0 days.

(21) Appl. No.: 09/700,851

(22) PCT Filed: May 19, 1999

(86) PCT No.: PCT/US99/11179

§ 371 (c)(1), (2), (4) Date: Nov. 3, 2003

(87) PCT Pub. No.: WO99/59629

PCT Pub. Date: Nov. 25, 1999

Related U.S. Application Data

(60) Provisional application No. 60/086,570, filed on May 20, 1998.

(51) Int. Cl.
*A61K 39/00* (2006.01)
*A61K 39/40* (2006.01)
*A61K 39/02* (2006.01)

(52) U.S. Cl. .............. 424/133.1; 424/150.1; 424/236.1; 424/241.1; 435/70.21; 435/71.3; 435/328; 435/388.1; 435/388.4

(58) Field of Classification Search .............. 424/133.1, 424/150.1, 236.1, 241.1; 435/70.21, 71.3, 435/328, 388.1, 388.4
See application file for complete search history.

(56) References Cited

U.S. PATENT DOCUMENTS

| | | | |
|---|---|---|---|
| 5,512,282 | A | 4/1996 | Krivan et al. |
| 5,530,101 | A | 6/1996 | Queen et al. |
| 5,585,089 | A | 12/1996 | Queen et al. |

FOREIGN PATENT DOCUMENTS

| | | | |
|---|---|---|---|
| CA | 2078716 | | 3/1994 |
| CA | 2163716 | | 5/1997 |
| ES | 2183144 | T3 | 3/2003 |
| JP | 05-304987 | A | 11/1993 |
| JP | 06-503963 | A | 5/1994 |
| JP | 07-504808 | A | 6/1995 |
| JP | 2003-521219 | A | 7/2003 |
| WO | WO95/22349 | A1 | 8/1995 |
| WO | WO96/28731 | A1 | 9/1996 |
| WO | WO96/30043 | A1 | 10/1996 |
| WO | WO 98/20903 | A1 | 5/1998 |
| WO | WO 99/32645 | A1 | 7/1999 |

OTHER PUBLICATIONS

Nakao et al., "Monoclonal Antibody to Shiga Toxin 2 Which Blocks Receptor Binding and Neutralizes Cytotoxicity," *Infection and Immunity*, 67(11):5717-5722 (1999).

Downes et al., "Affinity Purification and Characterization of Shiga-Like Toxin II and Production of Toxin-Specific Monoclonal Antibodies," *Infection and Immunity*, 56(8):1926-1933 (1988).

Hii et al., "Development of Verotoxin 2- and Verotoxin 2 Variant (VT2v)-Specific Oligonucleotide Probes on the Basis of the Nucleotide Sequence of the B Cistron of VT2v from *Escherichia coli* E32511 and B2F1," *J. Clinical Microbiology*, 29(12):2704-2709 (1991).

Perera et al., "Isolation and Characterization of Monoclonal Antibodies to Shiga-Like Toxin II of Enterohemorrhagic *Escherichia coli* and Use of Monoclonal Antibodies in a Colony Enzyme-Linked Immunosorbent Assay," *J. Clin. Microbiology*, 26(10):2127-2131 (1988).

Schmitt et al, "Two Copies of Shiga-Like Toxin II-Related Genes Common in Enterohemorrhagic *Escherichia coli* Strains are Responsible for the Antigenic Heterogeneity of the O157:h- Strain E32511," *Infection and Immunity*, 59(3):1065-1073 (1991).

Hii et al., "Development of Verotoxin 2- and Verotoxin 2 Variant (VT2v)-Specific Oligonucleotide Probes on the Basis of the Nucleotide Sequence of the B Cistron of VT2v from *Escherichia coli* E32511 and B2F1," *Journal of Clinical Microbiology*, 29(12):2704-2709 (1991).

Lindgren et al., "Virulence of Enterohemorrhagic *Escherichia coli* 091:H21 Clinical Isolates in an Orally Infected Mouse Model," *Infection and Immunity*, 61(9)3832-3842 (1993).

Morooka et al., "Anti-verocytotoxin (VT)1, VT2 and VT2c antibodies in commercial intravenous immune globulins in Japan," *Acta Paediatrica Japonica*, 38:294-295 (1996).

Perera et al., "Isolation and Characterization of Monoclonal Antibodies to Shiga-Like Toxin II of Enterohemorrhagic *Escherichia coli* and Use of the Monoclonal Antibodies in a Colony Enzyme-Linked Immunosorbent Assay," *J. Clinical Microbiology*, 26(10):2127-2131 (1988).

Schmitt et al.., "Two Copies of Shiga-Like Toxin II-Related Genes Common in Enterohemorrhagic *Escherichia coli* Strains Are Responsible for the Antigenic Heterogeneity of the O157:H-Strain E32511," *Infection and Immunity*, 59(3):1065-1073 (1991).

Wadolkowski et al., "Acute Renal Tubular Necrosis and Death of Mice Orally Infected with *Escherichia coli* Strains That Produce Shiga-Like Toxin Type II," *Infection and Immunity*, 58(12):3959-3965 (1990).

*Primary Examiner*—Rodney P. Swartz
(74) *Attorney, Agent, or Firm*—Townsend and Townsend and Crew LLP

(57) ABSTRACT

The invention provides humanized antibodies that specifically bind to, and preferably, neutralize, verotoxin II (VT2). The antibodies are useful for treating patients suffering from, or at risk of suffering, toxic effects of verotoxin.

27 Claims, 9 Drawing Sheets

```
                                        30                                                60
ATG AAC TTT GTG CTC AGC TCG ATT TTC CTT GCC CTC ATT TTA AAA GGA GTC CAG TGT GAA
 M   N   F   V   L   S   S   I   F   L   A   L   I   L   K   G   V   Q   C   E

                                        90                                               120
GTG CAG CTG GTG GAG TCG GGG GGA GGC TTA GTG AAG CCT GGA GGG CCC CTG AAA CTC TCC
 V   Q   L   V   E   S   G   G   G   L   V   K   P   G   G   P   L   K   L   S

                                       150                                               180
TGT GCA GCC TCT GGA TTC ACT TTC AGT AGT TAT GGC ATG TCT TGG GTT CGC CAG ACT CCG
 C   A   A   S   G   F   T   F   S   S   Y   G   M   S   W   V   R   Q   T   P

                                       210                                               240
GAG AAG AGG CTG GAG TGG GTC GCA ACC ATT AGT ACT GGT GGT AGT TAC ACC TAC TAC CCA
 E   K   R   L   E   W   V   A   T   I   S   T   G   G   S   Y   T   Y   Y   P

                                       270                                               300
GAC AGT GTG AAG GGT CGA TTC ACC ATC TCC AGA GAC AAT GCC AAG AAC GCC CTG TAT CTG
 D   S   V   K   G   R   F   T   I   S   R   D   N   A   K   N   A   L   Y   L

                                       330                                               360
CAA ATG AGC AGT CTG AGG TCT GAG GAC ACG GCC ATA TAT TAC TGT GCA AGA CGG GGG GAC
 Q   M   S   S   L   R   S   E   D   T   A   I   Y   Y   C   A   R   R   G   D

                                       390
GCA TGG GGT AAC TTG GAC TAC TGG GGT CAA GGA ACC TCT GTC ACC GTC TCC TCA
 A   W   G   N   L   D   Y   W   G   Q   G   T   S   V   T   V   S   S
```

FIG. 1(A).

```
                                    30                                                60
ATG GTT TTC ACA CCT CAG ATA CTT GGA CTT ATG CTT TTT TGG ATT TCA GCC TCC AGA GGT
 M   V   F   T   P   Q   I   L   G   L   M   L   F   W   I   S   A   S   R   G

                                    90                                               120
GAT GTT GTG CTA ACT CAG TCT CCA GCC ACC CTG TCT GTG ACT CCA GGA GAT AGC GTC AGT
 D   V   V   L   T   Q   S   P   A   T   L   S   V   T   P   G   D   S   V   S

                                   150                                               180
CTT TCC TGC AGG GCC AGT CAA ACT ATT AGC AAC AAC CTA CAC TGG TAT CAA CAC AAA TCA
 L   S   C   R   A   S   Q   T   I   S   N   N   L   H   W   Y   Q   H   K   S

                                   210                                               240
CAT GAG TCT CCA AGG CTT CTC ATC AAG TCT GCT TCC CAG TCC ATC TCT GGG ATC CCC TCC
 H   E   S   P   R   L   L   I   K   S   A   S   Q   S   I   S   G   I   P   S

                                   270                                               300
AGG TTC AGT GGC AGT GGA TCA GGG ACA GAT TTC ACT CTC AGT ATC AAC AGT GTG GAA ACT
 R   F   S   G   S   G   S   G   T   D   F   T   L   S   I   N   S   V   E   T

                                   330                                               360
GAA GAT TTT GGA ATG TAT TTC TGT CAA CAG AGT TAC AGC TGG CCG CTC ACG TTC GGT GCT
 E   D   F   G   M   Y   F   C   Q   Q   S   Y   S   W   P   L   T   F   G   A

GGG ACC AAG CTG GAG CTG AAA
 G   T   K   L   E   L   K
```

FIG. 1(B).

```
                                     30                                                60
ATG AAC TTT GTG CTC AGC TCG ATT TTC CTT GCC CTC ATT TTA AAA GGA GTC CAG TGT GAA
 M   N   F   V   L   S   S   I   F   L   A   L   I   L   K   G   V   Q   C   E

                                     90                                               120
GTG CAA CTG GTG GAG TCG GGG GGA GGC TTA GTG CAG CCT GGA GGG TCC CTG AGA CTC TCC
 V   Q   L   V   E   S   G   G   G   L   V   Q   P   G   G   S   L   R   L   S

                                    150                                               180
TGT GCA GCC TCT GGA TTC ACT TTC AGT AGT TAT GGC ATG TCT TGG GTT CGC CAG GCT CCG
 C   A   A   S   G   F   T   F   S   S   Y   G   M   S   W   V   R   Q   A   P

                                    210                                               240
GGT AAG GGT CTG GAG TGG GTC GCA ACC ATT AGT ACT GGT GGT AGT TAC ACC TAC TAC CCA
 G   K   G   L   E   W   V   A   T   I   S   T   G   G   S   Y   T   Y   Y   P

                                    270                                               300
GAC AGT GTG AAG GGT CGA TTC ACC ATC TCC AGA GAC AAT TCC AAG AAC ACC CTG TAT CTG
 D   S   V   K   G   R   F   T   I   S   R   D   N   S   K   N   T   L   Y   L

                                    330                                               360
CAA ATG AAC AGT CTG AGG GCT GAG GAC ACG GCC GTA TAT TAC TGT GCA AGA CGG GGG GAC
 Q   M   N   S   L   R   A   E   D   T   A   V   Y   Y   C   A   R   R   G   D

                                    390                                               420
GCA TGG GGT AAC TTG GAC TAC TGG GGT CAA GGA ACC TTA GTC ACC GTC TCC TCA
 A   W   G   N   L   D   Y   W   G   Q   G   T   L   V   T   V   S   S
```

*FIG. 2(A).*

```
                                            30                                                 60
ATG GTT TTC ACA CCT CAG ATA CTT GGA CTT ATG CTT TTT TGG ATT TCA GCC TCC AGA GGT
 M   V   F   T   P   Q   I   L   G   L   M   L   F   W   I   S   A   S   R   G

                                            90                                                120
GAA ATT GTG CTA ACT CAG TCT CCA GCC ACC CTG TCT GTG TCT CCA GGA GAA AGA GCC ACT
 E   I   V   L   T   Q   S   P   A   T   L   S   V   S   P   G   E   R   A   T

                                           150                                                180
CTT TCC TGC AGG GCC AGT CAA ACT ATT AGC AAC AAC CTA CAC TGG TAT CAA CAA AAA CCA
 L   S   C   R   A   S   Q   T   I   S   N   N   L   H   W   Y   Q   Q   K   P

                                           210                                                240
GGT CAG GCT CCA AGG CTT CTC ATC AAG TCT GCT TCC CAG TCC ATC TCT GGG ATA CCC GCC
 G   Q   A   P   R   L   L   I   K   S   A   S   Q   S   I   S   G   I   P   A

                                           270                                                300
AGG TTC AGT GGC AGT GGA TCA GGG ACA GAT TTC ACT CTC ACT ATC AGC AGT CTG GAA TCT
 R   F   S   G   S   G   S   G   T   D   F   T   L   T   I   S   S   L   E   S

                                           330                                                360
GAA GAT TTT GCA GTG TAT TAC TGT CAA CAG AGT TAC AGT TGG CCG CTC ACG TTC GGT CAA
 E   D   F   A   V   Y   Y   C   Q   Q   S   Y   S   W   P   L   T   F   G   Q

GGG ACC AAG GTG GAG ATC AAA
 G   T   K   V   E   I   K
```

FIG. 2(B).

SEQUENCE LISTING

```
<160> NUMBER OF SEQ ID NOS: 10

<210> SEQ ID NO 1
<211> LENGTH: 414
<212> TYPE: DNA
<213> ORGANISM: Mus musculus
<220> FEATURE:
<221> NAME/KEY: CDS
<222> LOCATION: (1)..(414)
<220> FEATURE:
<223> OTHER INFORMATION: Figure 1(A): Heavy chain variable region of
      mouse antibody VTm1.1 (MuVTm1.1).

<400> SEQUENCE: 1

atg aac ttt gtg ctc agc tcg att ttc ctt gcc ctc att tta aaa gga       48
Met Asn Phe Val Leu Ser Ser Ile Phe Leu Ala Leu Ile Leu Lys Gly
  1               5                  10                  15

gtc cag tgt gaa gtg cag ctg gtg gag tcg ggg gga ggc tta gtg aag       96
Val Gln Cys Glu Val Gln Leu Val Glu Ser Gly Gly Gly Leu Val Lys
             20                  25                  30

cct gga ggg ccc ctg aaa ctc tcc tgt gca gcc tct gga ttc act ttc      144
Pro Gly Gly Pro Leu Lys Leu Ser Cys Ala Ala Ser Gly Phe Thr Phe
         35                  40                  45

agt agt tat ggc atg tct tgg gtt cgc cag act ccg gag aag agg ctg      192
Ser Ser Tyr Gly Met Ser Trp Val Arg Gln Thr Pro Glu Lys Arg Leu
     50                  55                  60

gag tgg gtc gca acc att agt act ggt ggt agt tac acc tac tac cca      240
Glu Trp Val Ala Thr Ile Ser Thr Gly Gly Ser Tyr Thr Tyr Tyr Pro
 65                  70                  75                  80

gac agt gtg aag ggt cga ttc acc atc tcc aga gac aat gcc aag aac      288
Asp Ser Val Lys Gly Arg Phe Thr Ile Ser Arg Asp Asn Ala Lys Asn
                 85                  90                  95

gcc ctg tat ctg caa atg agc agt ctg agg tct gag gac acg gcc ata      336
Ala Leu Tyr Leu Gln Met Ser Ser Leu Arg Ser Glu Asp Thr Ala Ile
            100                 105                 110

tat tac tgt gca aga cgg ggg gac gca tgg ggt aac ttg gac tac tgg      384
Tyr Tyr Cys Ala Arg Arg Gly Asp Ala Trp Gly Asn Leu Asp Tyr Trp
        115                 120                 125

ggt caa gga acc tct gtc acc gtc tcc tca                              414
Gly Gln Gly Thr Ser Val Thr Val Ser Ser
    130                 135


<210> SEQ ID NO 2
<211> LENGTH: 138
<212> TYPE: PRT
<213> ORGANISM: Mus musculus
<220> FEATURE:
<223> OTHER INFORMATION: Figure 1(A): Heavy chain variable region of
      mouse antibody VTm1.1 (MuVTm1.1).

<400> SEQUENCE: 2

Met Asn Phe Val Leu Ser Ser Ile Phe Leu Ala Leu Ile Leu Lys Gly
  1               5                  10                  15

Val Gln Cys Glu Val Gln Leu Val Glu Ser Gly Gly Gly Leu Val Lys
             20                  25                  30

Pro Gly Gly Pro Leu Lys Leu Ser Cys Ala Ala Ser Gly Phe Thr Phe
         35                  40                  45
```

-continued

Ser Ser Tyr Gly Met Ser Trp Val Arg Gln Thr Pro Glu Lys Arg Leu
50 55 60

Glu Trp Val Ala Thr Ile Ser Thr Gly Gly Ser Tyr Thr Tyr Tyr Pro
65 70 75 80

Asp Ser Val Lys Gly Arg Phe Thr Ile Ser Arg Asp Asn Ala Lys Asn
85 90 95

Ala Leu Tyr Leu Gln Met Ser Ser Leu Arg Ser Glu Asp Thr Ala Ile
100 105 110

Tyr Tyr Cys Ala Arg Arg Gly Asp Ala Trp Gly Asn Leu Asp Tyr Trp
115 120 125

Gly Gln Gly Thr Ser Val Thr Val Ser Ser
130 135

<210> SEQ ID NO 3
<211> LENGTH: 381
<212> TYPE: DNA
<213> ORGANISM: Mus musculus
<220> FEATURE:
<221> NAME/KEY: CDS
<222> LOCATION: (1)..(381)
<220> FEATURE:
<223> OTHER INFORMATION: Figure 1(B): Light chain variable region of mouse VTm1.1 antibody (MuVTm1.1).

<400> SEQUENCE: 3 atg gtt ttc aca cct cag ata ctt gga ctt atg ctt ttt tgg att tca 48
Met Val Phe Thr Pro Gln Ile Leu Gly Leu Met Leu Phe Trp Ile Ser
1 5 10 15 gcc tcc aga ggt gat gtt gtg cta act cag tct cca gcc acc ctg tct 96
Ala Ser Arg Gly Asp Val Val Leu Thr Gln Ser Pro Ala Thr Leu Ser
20 25 30 gtg act cca gga gat agc gtc agt ctt tcc tgc agg gcc agt caa act 144
Val Thr Pro Gly Asp Ser Val Ser Leu Ser Cys Arg Ala Ser Gln Thr
35 40 45 att agc aac aac cta cac tgg tat caa cac aaa tca cat gag tct cca 192
Ile Ser Asn Asn Leu His Trp Tyr Gln His Lys Ser His Glu Ser Pro
50 55 60 agg ctt ctc atc aag tct gct tcc cag tcc atc tct ggg atc ccc tcc 240
Arg Leu Leu Ile Lys Ser Ala Ser Gln Ser Ile Ser Gly Ile Pro Ser
65 70 75 80 agg ttc agt ggc agt gga tca ggg aca gat ttc act ctc agt atc aac 288
Arg Phe Ser Gly Ser Gly Ser Gly Thr Asp Phe Thr Leu Ser Ile Asn
85 90 95 agt gtg gaa act gaa gat ttt gga atg tat ttc tgt caa cag agt tac 336
Ser Val Glu Thr Glu Asp Phe Gly Met Tyr Phe Cys Gln Gln Ser Tyr
100 105 110 agc tgg ccg ctc acg ttc ggt gct ggg acc aag ctg gag ctg aaa 381
Ser Trp Pro Leu Thr Phe Gly Ala Gly Thr Lys Leu Glu Leu Lys
115 120 125

<210> SEQ ID NO 4
<211> LENGTH: 127
<212> TYPE: PRT
<213> ORGANISM: Mus musculus
<220> FEATURE:
<223> OTHER INFORMATION: Figure 1(B): Light chain variable region of mouse VTm1.1 antibody (MuVTm1.1).

<400> SEQUENCE: 4

Met Val Phe Thr Pro Gln Ile Leu Gly Leu Met Leu Phe Trp Ile Ser
1 5 10 15

Ala Ser Arg Gly Asp Val Val Leu Thr Gln Ser Pro Ala Thr Leu Ser

-continued

```
            20                  25                  30

Val Thr Pro Gly Asp Ser Val Ser Leu Ser Cys Arg Ala Ser Gln Thr
        35                  40                  45

Ile Ser Asn Asn Leu His Trp Tyr Gln His Lys Ser His Glu Ser Pro
    50                  55                  60

Arg Leu Leu Ile Lys Ser Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Ser Tyr
            100                 105                 110

Ser Trp Pro Leu Thr Phe Gly Ala Gly Thr Lys Leu Glu Leu Lys
        115                 120                 125


<210> SEQ ID NO 5
<211> LENGTH: 414
<212> TYPE: DNA
<213> ORGANISM: Mus musculus
<220> FEATURE:
<221> NAME/KEY: CDS
<222> LOCATION: (1)..(414)
<220> FEATURE:
<223> OTHER INFORMATION: Figure 2(A): Heavy chain variable region of
      humanized VTm1.1 antibody (HuVTm1.1).

<400> SEQUENCE: 5

atg aac ttt gtg ctc agc tcg att ttc ctt gcc ctc att tta aaa gga       48
Met Asn Phe Val Leu Ser Ser Ile Phe Leu Ala Leu Ile Leu Lys Gly
1               5                   10                  15

gtc cag tgt gaa gtg caa ctg gtg gag tcg ggg gga ggc tta gtg cag       96
Val Gln Cys Glu Val Gln Leu Val Glu Ser Gly Gly Gly Leu Val Gln
            20                  25                  30

cct gga ggg tcc ctg aga ctc tcc tgt gca gcc tct gga ttc act ttc      144
Pro Gly Gly Ser Leu Arg Leu Ser Cys Ala Ala Ser Gly Phe Thr Phe
        35                  40                  45

agt agt tat ggc atg tct tgg gtt cgc cag gct ccg ggt aag ggt ctg      192
Ser Ser Tyr Gly Met Ser Trp Val Arg Gln Ala Pro Gly Lys Gly Leu
    50                  55                  60

gag tgg gtc gca acc att agt act ggt ggt agt tac acc tac tac cca      240
Glu Trp Val Ala Thr Ile Ser Thr Gly Gly Ser Tyr Thr Tyr Tyr Pro
65                  70                  75                  80

gac agt gtg aag ggt cga ttc acc atc tcc aga gac aat tcc aag aac      288
Asp Ser Val Lys Gly Arg Phe Thr Ile Ser Arg Asp Asn Ser Lys Asn
                85                  90                  95

acc ctg tat ctg caa atg aac agt ctg agg gct gag gac acg gcc gta      336
Thr Leu Tyr Leu Gln Met Asn Ser Leu Arg Ala Glu Asp Thr Ala Val
            100                 105                 110

tat tac tgt gca aga cgg ggg gac gca tgg ggt aac ttg gac tac tgg      384
Tyr Tyr Cys Ala Arg Arg Gly Asp Ala Trp Gly Asn Leu Asp Tyr Trp
        115                 120                 125

ggt caa gga acc tta gtc acc gtc tcc tca                              414
Gly Gln Gly Thr Leu Val Thr Val Ser Ser
    130                 135


<210> SEQ ID NO 6
<211> LENGTH: 138
<212> TYPE: PRT
<213> ORGANISM: Mus musculus
<220> FEATURE:
<223> OTHER INFORMATION: Figure 2(A): Heavy chain variable region of
      humanized VTm1.1 antibody (HuVTm1.1).
```

-continued

<400> SEQUENCE: 6

```
Met Asn Phe Val Leu Ser Ser Ile Phe Leu Ala Leu Ile Leu Lys Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Tyr Gly Met Ser Trp Val Arg Gln Ala Pro Gly Lys Gly Leu
     50                  55                  60

Glu Trp Val Ala Thr Ile Ser Thr Gly Gly Ser Tyr Thr Tyr Tyr Pro
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Arg Gly Asp Ala Trp Gly Asn Leu Asp Tyr Trp
        115                 120                 125

Gly Gln Gly Thr Leu Val Thr Val Ser Ser
    130                 135
```

<210> SEQ ID NO 7
<211> LENGTH: 381
<212> TYPE: DNA
<213> ORGANISM: Mus musculus
<220> FEATURE:
<221> NAME/KEY: CDS
<222> LOCATION: (1)..(381)
<220> FEATURE:
<223> OTHER INFORMATION: igure 2(B): Light chain variable region of humanized VTm1.1 antibody (HuVTm1.1) .

<400> SEQUENCE: 7

```
atg gtt ttc aca cct cag ata ctt gga ctt atg ctt ttt tgg att tca       48
Met Val Phe Thr Pro Gln Ile Leu Gly Leu Met Leu Phe Trp Ile Ser
  1               5                  10                  15

gcc tcc aga ggt gaa att gtg cta act cag tct cca gcc acc ctg tct       96
Ala Ser Arg Gly Glu Ile Val Leu Thr Gln Ser Pro Ala Thr Leu Ser
             20                  25                  30

gtg tct cca gga gaa aga gcc act ctt tcc tgc agg gcc agt caa act      144
Val Ser Pro Gly Glu Arg Ala Thr Leu Ser Cys Arg Ala Ser Gln Thr
         35                  40                  45

att agc aac aac cta cac tgg tat caa caa aaa cca ggt cag gct cca      192
Ile Ser Asn Asn Leu His Trp Tyr Gln Gln Lys Pro Gly Gln Ala Pro
     50                  55                  60

agg ctt ctc atc aag tct gct tcc cag tcc atc tct ggg ata ccc gcc      240
Arg Leu Leu Ile Lys Ser Ala Ser Gln Ser Ile Ser Gly Ile Pro Ala
 65                  70                  75                  80

agg ttc agt ggc agt gga tca ggg aca gat ttc act ctc act atc agc      288
Arg Phe Ser Gly Ser Gly Ser Gly Thr Asp Phe Thr Leu Thr Ile Ser
                 85                  90                  95

agt ctg gaa tct gaa gat ttt gca gtg tat tac tgt caa cag agt tac      336
Ser Leu Glu Ser Glu Asp Phe Ala Val Tyr Tyr Cys Gln Gln Ser Tyr
            100                 105                 110

agt tgg ccg ctc acg ttc ggt caa ggg acc aag gtg gag atc aaa          381
Ser Trp Pro Leu Thr Phe Gly Gln Gly Thr Lys Val Glu Ile Lys
        115                 120                 125
```

<210> SEQ ID NO 8
<211> LENGTH: 127
<212> TYPE: PRT

-continued

<213> ORGANISM: Mus musculus
<220> FEATURE:
<223> OTHER INFORMATION: Figure 2(B): Light chain variable region of humanized VTm1.1 antibody (HuVTm1.1) .

<400> SEQUENCE: 8

```
Met Val Phe Thr Pro Gln Ile Leu Gly Leu Met Leu Phe Trp Ile Ser
  1               5                  10                  15

Ala Ser Arg Gly Glu Ile Val Leu Thr Gln Ser Pro Ala Thr Leu Ser
             20                  25                  30

Val Ser Pro Gly Glu Arg Ala Thr Leu Ser Cys Arg Ala Ser Gln Thr
         35                  40                  45

Ile Ser Asn Asn Leu His Trp Tyr Gln Gln Lys Pro Gly Gln Ala Pro
     50                  55                  60

Arg Leu Leu Ile Lys Ser Ala Ser Gln Ser Ile Ser Gly Ile Pro Ala
 65                  70                  75                  80

Arg Phe Ser Gly Ser Gly Ser Gly Thr Asp Phe Thr Leu Thr Ile Ser
                 85                  90                  95

Ser Leu Glu Ser Glu Asp Phe Ala Val Tyr Tyr Cys Gln Gln Ser Tyr
            100                 105                 110

Ser Trp Pro Leu Thr Phe Gly Gln Gly Thr Lys Val Glu Ile Lys
        115                 120                 125
```

<210> SEQ ID NO 9
<211> LENGTH: 123
<212> TYPE: PRT
<213> ORGANISM: Homo sapiens
<220> FEATURE:
<223> OTHER INFORMATION: heavy chain variable region of the GF4/1.1 antibody

<400> SEQUENCE: 9

```
Glu Val Gln Val Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Lys Tyr
             20                  25                  30

Ala Met Ser Trp Val Arg Gln Ala Pro Gly Lys Gly Leu Glu Trp Val
         35                  40                  45

Ser Gly Ile Ser Ala Ser Gly Glu Asn Thr Tyr Tyr Ala Asp Pro Val
     50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Asp Asp Thr Ala Met Tyr Tyr Cys
                 85                  90                  95

Ala Lys Gly Gly Arg Gln Trp Val Val Leu Gly Tyr Phe Phe Asp Ser
            100                 105                 110

Trp Gly Gln Gly Thr Leu Val Thr Val Ser Ser
        115                 120
```

<210> SEQ ID NO 10
<211> LENGTH: 110
<212> TYPE: PRT
<213> ORGANISM: Homo sapiens
<220> FEATURE:
<223> OTHER INFORMATION: light chain variable region of the GF4/1.1 antibody

<400> SEQUENCE: 10

```
Glu Ile Leu Met Thr Gln Ser Pro Ala Thr Leu Ser Val Ser Pro Gly
  1               5                  10                  15
```

-continued

```
Glu Arg Val Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Asn Ser Leu Gln Ser
65                  70                  75                  80

Glu Asp Phe Ala Leu Tyr Tyr Cys His Glu Tyr Asn Gly Trp Pro Pro
                85                  90                  95

Trp Thr Phe Gly Gln Gly Thr Lys Val Glu Ile Lys Arg Thr
            100                 105                 110
```

HUMANIZED ANTIBODIES THAT RECOGNIZE VEROTOXIN II AND CELL LINE PRODUCING SAME

CROSS REFERENCE TO RELATED APPLICATION

This application is the US national phase of PCT/US99/11179, filed May 20, 1999, which is a non-provisional of and derives priority from U.S. Ser. No. 60/086,570 filed May 20, 1998, which is incorporated by reference in its entirety for all purposes.

REFERENCE TO A "SEQUENCE LISTING"

The Sequence Listing written in file 019026-000110US_SEQLST.txt is 15,708 bytes, and was created on Jun. 8, 2009, for the application filed herewith, Yoh-ichi Matsumoto et al. "Humanized Antibodies That Recognize Verotoxin II and Cell Line Producing The Same." The information contained in this file is hereby incorporated by reference.

FIELD OF INVENTION

The present invention relates generally to the combination of recombinant DNA and monoclonal antibody technologies for developing novel biologics and, more particularly, for example, to the production of non-immunogenic (in humans) immunoglobulins specific for the Verotoxin II (VT2) antigen and Verotoxin II variant antigens (VT2V) and their uses in vitro and in vivo. The present invention also relates more specifically to humanized monoclonal antibodies against VT2 which are capable of neutralizing VT2 and VT2V, polynucleotide sequences encoding the antibodies, a method of producing the antibodies, pharmaceutical compositions comprising the antibody as an active ingredient, therapeutic agents for treating Verotoxin Producing *E. coli* (VTEC) infection and Hemolytic Uremic Syndrome (HUS) comprising the antibody as an active ingredient, and methods of treating such diseases.

BACKGROUND OF THE INVENTION

Verotoxin (VT), also known as Shiga-like toxin (SLT), is known to cause bloody diarrhea and development of hemolytic uremic syndrome in Verotoxin Producing *E. coli* (VTEC) infection. One of the etiologic agents of VTEC infection is the virulent *E. coli* 0157. VT may also be produced by bacteria other than those that cause VTEC infection which may also result in a toxic syndrome in humans. In children or elderly adults with reduced immune responses, VT produced by bacteria growing in the intestines may get into the bloodstream by disrupting the intestinal epithelial cells. This may induce Hemolytic Uremic Syndrome (HUS) which is characterized by renal dysfunction and sometimes brain damage (see, e.g., Karmali, M. et al., *The Lancet,* 1, 619-620 (1983); Siegler, R., *The Journal of Pediatrics,* 125, 511-518 (1994)). To date, there exists no effective drug for these toxic syndromes. Antibiotics have not demonstrated efficacy to prevent the progression of the toxic syndromes (see, e.g., Carter, A. et al., *The New England Journal of Medicine,* 316, 1496-1500 (1987); Griffen, P. et al., *Annals of Internal Medicine,* 109, 705-712 (1988)). This might be because of the release of VT from bacteria killed by the antibiotics and the ineffectiveness of antibiotics against VT.

There are two types of Verotoxin, (or Shiga-like toxin) Verotoxin I (VT1 or SLT-1) and Verotoxin II (VT2 or SLT-2).

(See, O'Brien et al., *Curr. Top. Microbiol. Immunol.,* 180, 65-94. (1992)). VT2 producing *E. coli* have been isolated from patients suffering from VTEC infecion. (See, Russmann et al., *J. Med. Microbiol.,* 40(5), 338-343 (1994)). Ostroff et al., *J. Infect. Dis.* 160, 994-998 (1989) and Kleanthous et al., *Arch. Dis. child.* 65, 722-727 (1990) report that *E. coli* 0157 strains that contained VT2 but not VT1 were more frequently associated with HUS. There are additional VT2 variants (VT2V) that have also been isolated clinically. (See, e.g., *Microb. Pathog.,* 8, 47-60 (1990); FEBS Lett., 79, 27-30 (1991); *Microb. Pathog.,* 5, 419-426 (1988); and *J. Bacteriol.,* 170, 4223-4230 (1988)). Armstrong et al., *J. Infect. Dis.,* 171(4), 1042-1045 (1995), have tested a VT absorbent in clinical trials, however, this drug works only in the intestine and is not available to absorb VT that has reached the bloodstream. A γ-globulin preparation showed very low neutralization activity for VT2 in comparison with that for VT1 (Ashkenazi, S. et al., *The Journal of Pediatrics,* 113, 1008-1014 (1988); Morooka, T. et al., *Acta Paediatrica Japonica,* 38, 294-295 (1996)). A mouse monoclonal antibody which neutralizes VT2 has been reported. However, this antibody was reported to show a relatively low binding affinity for VT2V (, Schmitt, C. et al., *Infection and Immunity,* 59, 1065-1073 (1991)).

Further, the use of murine monoclonal antibodies such as those described above have certain drawbacks in human treatment, particularly in repeated therapeutic regimens as explained below. Mouse monoclonal antibodies, for example, tend to have a short half-life in humans, and lack other important immunoglobulin functional characteristics when used in humans.

In addition, murine monoclonal antibodies contain substantial amino acid sequences that will be immunogenic when injected into a human patient. Numerous studies have shown that, after injection of a foreign antibody, the immune response elicited by a patient against the injected antibody can be quite strong, essentially eliminating the antibody's therapeutic utility after an initial treatment. Moreover, if mouse or other antigenic (to humans) monoclonal antibodies are used to treat various human diseases, subsequent treatments with unrelated mouse antibodies may be ineffective or even dangerous in themselves, because of cross-reactivity.

While the production of so-called "chimeric antibodies" (e.g., mouse variable regions joined to human constant regions) has proven somewhat successful, a significant immunogenicity problem remains. In general, the production of human immunoglobulins reactive with VT2 antigen with high affinity, as with many antigens, would be extremely difficult using typical human monoclonal antibody production techniques.

Thus, there is a need for improved forms of humanized immunoglobulins specific for VT2 antigen that are substantially non-immunogenic in humans, yet easily and economically produced in a manner suitable for therapeutic formulation and other uses. The present invention fulfills these and other needs.

SUMMARY OF THE INVENTION

The invention provides humanized antibodies that specifically bind to VT2 and/or VT2 variant. Some such antibodies specifically bind to the B subunit of VT2 and/or the B subunit of VT2 variant. Some such antibodies neutralizes VT2 and/or VT2 variant. Preferred antibodies neutralized VT2 and/or VT2 variants such as to provide at least 50%, 75%, 95% or 100% protection against mice or other mammalian subject challenged with 10 $LD_{50}$ of VT2 or VT2 variant.

Some humanized antibodies are a humanized form of mouse antibody VTm1.1, the mouse antibody being characterized by a light chain variable region shown in FIG. 1B and a heavy chain variable region shown in FIG. 1A.

The invention further provides antibodies that competes compete with mouse antibody VTm1.1 for specific binding to VT2 and/or VT2 variant.

Some of the humanized antibodies, as described above, comprise complementarity determining regions from the mouse VTm1.1 antibody and heavy and light chain variable region frameworks from the human GF4 antibody heavy and light chain frameworks, provided that at least one position selected from the group consisting of L49, H29, H30, H49 and H98, is occupied by the amino acid present in the equivalent position of the mouse VTm1.1 antibody heavy or light chain variable region framework. Such humanized antibodies specifically bind to verotoxin II with an affinity constant between $10^7$ $M^{-1}$ and three, five or ten-fold the affinity of the mouse VTm1.1 antibody.

In some humanized antibodies described in the previous paragraph, each position selected from the group consisting of L49, H29, H30, H49 and H98 is occupied by the amino acid present in the equivalent position of the mouse VTm1.1 antibody heavy or light chain variable region framework.

In some of the above humanized antibodies, at least one position selected from the group L3, L4, L19, L76, L79, L85, H1, H4, H5, H79, H89 and H93 is occupied by an amino acid present in the equivalent position of a human antibody heavy or light chain consensus sequence. In some humanized antibodies each position selected from the group L3, L4, L19, L76, L79, L85, H1, H4, H5, H79, H89 and H93 is occupied by an amino acid present in the equivalent position of a human antibody heavy or light chain consensus sequence.

Some humanized antibodies comprise a heavy chain variable region shown in FIG. 2A and a light chain variable region shown in FIG. 2B provided that one or more positions selected from the group consisting of L49, H29, H30, H49, H98, L3, L4, L19, L76, L79, L85, H1, H4, H5, H79, H89, and H93 may be substituted as shown in Tables 2 and 3.

Some humanized antibodies comprise a heavy chain variable region shown in FIG. 2A and a light chain variable region shown in FIG. 2B.

Some humanized antibodies comprise a humanized heavy chain having at least 85% identity with the humanized heavy chain shown in FIG. 2A and a humanized light chain having at least 85% sequence identity with the humanized light chain showing in FIG. 2B, provided that at least one position selected from the group consisting of L49, H29, H30, H49 and H98, is occupied by the amino acid present in the equivalent position of the mouse VTm1.1 antibody heavy or light chain variable region framework.

Some of the humanized antibodies as described above comprise two pairs of light/heavy chain dimers, wherein each chain comprises a variable region and a constant region.

Some of the humanized antibodies as described above are a Fab fragment or a $F(ab')_2$.

Optionally, humanized antibodies, as described above, are provided in purified form.

Some humanized antibodies, as described above, have an $IgG_1$ immunoglobulin isotype.

The invention further provides methods of producing humanized VTm1.1 antibody. Such methods comprise culturing a cell line, which encodes heavy and light chain chains of any of the antibodies described above, whereby the humanized antibody is expressed; and recovering the humanized antibody expressed by the cell line. Some such methods further comprise mixing the antibody with a pharmaceutically acceptable carrier to produce a pharmaceutical composition.

The invention further provides pharmaceutical compositions comprising any of the antibodies described above and a pharmaceutically acceptable carrier. A preferred such composition comprises a humanized antibody comprising a heavy chain variable region shown in FIG. 2A and a light chain variable region shown in FIG. 2B. The invention further provides for the use of any of the antibodies described above in the manufacture of a medicament for the treatment of a patient suffering or at risk of toxic effects from a verotoxin.

The invention further provides methods of treating a patient suffering or at risk of toxic effects from a verotoxin, comprising administering to the patient an effective dosage of a human or humanized antibody that specifically binds to verotoxin II and/or verotoxin II variant. In some such methods, the antibody competes with mouse antibody VTm1.1 for specific binding to verotoxin II or verotoxin II variant. In some such methods, the humanized antibody specifically binds to VT2 and/or VT2 variant. In some such methods, the humanized antibody specifically binds to the B subunit of VT2 and/or VT2 variant. In some such methods, the humanized antibody specifically binds to VT2 and/or VT2 variant and neutralizes VT2 and/or VT2 variant. In some such methods, the humanized antibody specifically binds to the B subunit of VT2 and/or the B subunit of VT2 variant and neutralizes VT2 and/or VT2 variant. In some such methods, the antibody is a humanized antibody, which is a humanized form of the mouse VTm1.1 antibody. In some such methods, the antibody is a humanized antibody comprising a heavy chain variable region shown in FIG. 2A and a light chain variable region shown in FIG. 2B. In some such methods, the patient is infected with verotoxin producing *E. coli* and the antibody is administered therapeutically. In some such methods, the patient is at risk of infection by verotoxin producing *E. coli* and the antibody is administered prophylactically. Some such methods further comprise monitoring the patient for recovery from the toxic effects of verotoxin II or verotoxin II variant.

In a further aspect, the invention provides a cell line which produces any of the above described antibodies.

The present invention provides novel compositions useful, for example, in the treatment of Verotoxin Producing *E. coli* (VTEC) infection and Hemolytic Uremic Syndrome (HUS), the compositions containing humanized immunoglobulins specifically capable of binding to the B subunit of VT2 antigen and of neutralizing VT2 and VT2 variants. The immunoglobulins can have two pairs of light chain/heavy chain complexes, at least one chain comprising one or more mouse complementarity determining regions functionally joined to human framework region segments. For example, mouse complementarity determining regions, with or without additional naturally associated mouse amino acid residues, can be introduced into human framework regions to produce humanized immunoglobulins capable of binding to the antigen at affinity levels stronger than about $10^7$ $M^{-1}$. These humanized immunoglobulins will also be capable of blocking the binding of the CDR-donating mouse monoclonal antibody to VT2.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be utilized in substantially pure form in treating potentially toxic outcomes from VT2 or VT2V such as those produced during Verotoxin Producing *E. coli* (VTEC) infection and Hemolytic Uremic Syndrome (HUS). The humanized immunoglobulins or their complexes can be prepared in a pharmaceutically accepted dosage form, which will vary depending on the mode of administration.

BRIEF DESCRIPTION OF THE FIGURES

FIG. 1. The cDNA and translated amino acid sequences of the heavy chain (A) (SEQ ID NOs:1-2) and light chain (B) (SEQ ID NOs:3-4) variable regions of the mouse VTm1.1 antibody (MuVTm1.1). The complementary determining regions (CDRs) are underlined and the first amino acids of the mature chains are double underlined.

FIG. 2. The cDNA and translated amino acid sequences of the heavy chain (A) (SEQ ID NOs:5-6) and light chain (B) (SEQ ID NOs:7-8) variable regions of the humanized VTm1.1 antibody (HuVTm1.1). The complementarity determining regions (CDRs) are underlined and the first amino acids of the mature chains are double underlined.

DEFINITIONS

Figure 3:
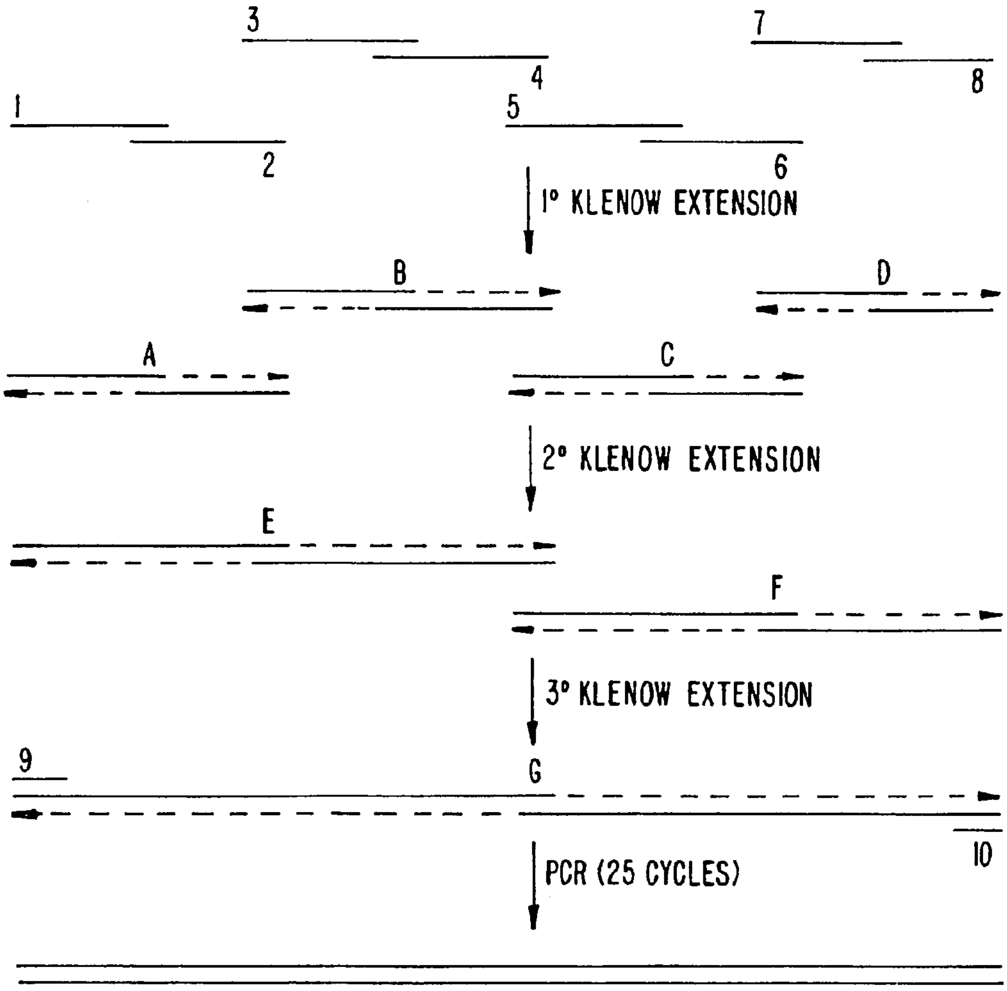
FIG. 3. Scheme for synthesis of humanized antibody variable region cDNA.

The phrase "substantially identical," in the context of two nucleic acids or polypeptides (e.g., DNAs encoding a humanized immunoglobulin or the amino acid sequence of the humanized immunoglobulin) refers to two or more sequences or subsequences that have at least about 80%, most preferably 85%, 90-95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequence that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering system of Kabat. Therefore, for antibodies, percent identity has a unique and well-defined meaning.

Amino acid sequences from the variable regions of the mature heavy and light chains of immunoglobulins are designated Hx and Lx respectively, where x is a number designating the position of an amino acid according to the scheme of Kabat, Sequences of Proteins of Immunological Interest (National Institutes of Health, Bethesda Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. For example, an amino acid at the L50 position of a human antibody occupies the equivalent position to an amino acid at position L50 of a mouse antibody.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Analogs of exemplified antibody sequences can be screened for retention of binding activity using phage display methods as described by, for example, Cesareni, *FEBS Lett* 307:66-70 (1992); Swimmer et al., *Proc. Natl. Acad. Sci. USA* 89:3756-60 (1992); Gram et al., *Proc. Natl. Acad. Sci. USA* 89:3576-80 (1992); Clackson et al., *Nature* 352:624-8 (1991); Scott & Smith, *Science* 249:386-90 (1990); Garrard et al., *Bio/Techniques* 9:1373-1377 (1991), which are incorporated herein by reference in their entirety for all purposes.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

Competition between antibodies is determined by an assay in which the immunoglobulin under test inhibits specific binding of a reference antibody to an antigenic determinant. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., *Molec. Immunol.* 25(1):7-15 (1988)); solid phase direct biotin-avidin EIA (Cheung et al., *Virology* 176:546-552

(1990)); and direct labeled RIA (Moldenhauer et al., *Scand. J. Immunol.* 32:77-82 (1990)). Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a designated antigenic target by at least 50 or 75%.

DETAILED DESCRIPTION OF THE INVENTION

In accordance with the present invention, humanized immunoglobulins specifically reactive with the B subunit of VT2 are provided. These immunoglobulins, which have binding affinities to the B subunit of VT2 of at least about $10^{-7}M^{-1}$ to $10^{10}M^{-1}$, and preferably $10^{8}$ $M^{-1}$ to $10^{10}M^{-1}$ or stronger, are capable of, e.g., neutralizing the toxicity of VT2 and VT2V (the VT2 antigens). The humanized immunoglobulins will have a human framework and will have one or more complementarity determining regions (CDR's) from an immunoglobulin, typically a mouse immunoglobulin, specifically reactive with VT2 antigens. In a preferred embodiment, one or more of the CDR's will come from the MuVTm1.1 antibody. Thus, the immunoglobulins of the present invention, which can be produced economically in large quantities, find use, for example, in the treatment of the toxic outcomes from Verotoxin Producing *E. coli* (VTEC) infection and Hemolytic Uremic Syndrome (HUS) in human patients by a variety of techniques.

The basic antibody structural unit is known to comprise a tetramer. Each tetramer is composed of two identical pairs of polypeptide chains, each pair having one "light" (about 25 kD) and one "heavy" chain (about 50-70 kD). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region and about 12 or more amino acids, with the heavy chain also including a "D" region or about 10 more amino acids. (See, generally, *Fundamental Immunology*, Paul, W., Ed., Chapter 7, pgs. 131-166, Raven Press, N.Y. (1984), which is incorporated herein by reference.)

The variable regions of each light/heavy chain pair form the antibody binding site. The chains all exhibit the same general structure of relatively conserved framework regions joined by three hypervariable regions, also called Complementarity Determining Regions or CDR's (see, "*Sequences of Proteins of Immunological Interest*," Kabat, E., et al., U.S. Department of Health and Human Services, (1987); and Chothia and Lesk, *J. Mol. Biol.,* 196, 901-917 (1987), which are incorporated herein by reference). The CDR's from the two chains of each pair are aligned by the framework regions, enabling binding to a specific epitope.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab, and F $(ab')_2$— as well as bifunctional hybrid antibodies (e.g., Lanzavecchia et al., Eur. J. Immunol. 17,105 (1987)) and in single chains (e.g., Huston et al., Proc. Natl. Acad. Sci. U.S.A., 85,58795883 (1988) and Bird et al., Science 242, 423-426 (1988), which are incorporated herein by reference). (See, generally, Hood et al., Immunology, Benjamin, N.Y., $2^{nd}$ ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ and $\gamma_3$. A typical therapeutic chimeric antibody is thus a hybrid protein consisting of the V or antigen-binding domain from a mouse antibody and the C or effector domain from a human antibody, although other mammalian species may be used.

As used herein, the term "framework region" refers to those portions of immunoglobulin light and heavy chain variable regions that are relatively conserved (i.e., other than the CDR's) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "humanized immunoglobulin" refers to an immunoglobulin comprising a human framework, at least one CDR from a non-human antibody, and in which any constant region present is substantially identical to a human immunoglobulin constant region, i.e., at least about 85-90%, preferably at least 95% identical. Hence, all parts of a humanized immunoglobulin, except possibly the CDR's, are substantially identical to corresponding parts of one or more native human immunoglobulin sequences. For example, a humanized immunoglobulin would not encompass a chimeric mouse variable region/human constant region antibody.

Humanized antibodies have at least three potential advantages over mouse and in some cases chimeric antibodies for use in human therapy:

Because the effector portion is human, it may interact better with the other parts of the human immune system (e.g., destroy the target cells more efficiently by complement-dependent cytotoxicity (CDC) or antibody-dependent cellular cytotoxicity (ADCC)).

The human immune system should not recognize the framework or C region of the humanized antibody as foreign, and therefore the antibody response against such an injected antibody should be less than against a totally foreign mouse antibody or a partially foreign chimeric antibody.

Injected mouse antibodies have been reported to have a half-life in the human circulation much shorter than the half-life of normal antibodies (Shaw, D. et al., *J. Immunol,* 138, 4534-4538 (1987)). Injected humanized antibodies will presumably have a half-life essentially identical to naturally occurring human antibodies, allowing smaller and less frequent doses to be given.

In one aspect, the present invention is directed to recombinant polynucleotides encoding the heavy and/or light chain CDR's from an immunoglobulin capable of binding the B subunit of VT2, such as monoclonal antibody MuVTm1.1. The polynucleotides encoding these regions will typically be joined to polynucleotides encoding appropriate human framework regions. As to the human framework region, a framework or variable region amino acid sequence of a CDR-providing non-human immunoglobulin is compared with corresponding sequences in a human immunoglobulin sequence collection, and a sequence having high homology is selected. Exemplary polynucleotides, which on expression code for the polypeptide chains comprising the heavy and light chain CDR's of monoclonal antibody MuVTm1.1 are included in FIG. 1. Due to codon degeneracy and non-critical amino-acid substitutions, other polynucleotide sequences can be readily substituted for those sequences, as detailed below. The design of humanized immunoglobulins may be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin):

the amino acid in the human framework region of the acceptor immunoglobulin is unusual for human immunoglobulin at that position, whereas the corresponding amino acid in the donor immunoglobulin is typical for human immunoglobulin in that position;

the position of the amino acid is immediately adjacent to one of the CDR's; or the amino acid is within about 3 Å of a CDR in a tertiary structure immunoglobulin model (see, Queen et al., op. cit., and Co et al., *Proc. Natl. Acad. Sci. USA* 88, 2869 (1991), respectively, both of which are incorporated herein by reference).

When each of the amino acids in the human framework region of the acceptor immunoglobulin and a corresponding amino acid in the donor immunoglobulin is unusual for human immunoglobulin at that position, such an amino acid is replaced by an amino acid typical for human immunoglobulin at that position.

For a detailed description of the production of humanized immunoglobulins see, Queen et al., op. cit., and Co et al., op. cit.

The polynucleotides will typically further include an expression control polynucleotide sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is presently the most common method of production, but cDNA sequences may also be utilized (see, European Patent Publication No. 0239400 and Riechmann, L. et al., *Nature,* 332, 323-327 (1988), both of which are incorporated herein by reference.)

Human constant region DNA sequences can be isolated in accordance with well known procedures from a variety of human cells, but preferably immortalized B-cells (see, Kabat op. cit. and WP 87/02671). The CDR's for producing the immunoglobulins of the present invention will be similarly derived from monoclonal antibodies capable of binding to VT2 antigens and produced in any convenient mammalian source, including, mice, rats, rabbits, or other vertebrate capable of producing antibodies by well known methods. Suitable source cells for polynucleotide sequences and host cells for immunoglobulin expression and secretion can be obtained from a number of sources, such as American Type Culture Collection (*Catalogue of Cell Lines and Hybridomas*, Fifth edition (1985) 10801 University Boulevard, Manassas, Va., U.S.A., which is incorporated herein by reference.

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized modifications of the present invention. In general, modifications of the genes may be readily accomplished by a variety of well-known techniques, such as site-directed mutagenesis (see, Gillman and Smith, *Gene* 8, 81-97 (1979) and Roberts S. et al., Nature 328, 731-734 (1987), both of which are incorporated herein by reference.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce $F(ab')_2$ fragments. Single chain antibodies may be produced by joining VL and VH with a DNA linker (see Huston et al., op cit., and Bird et al., op cit.). Also because like many genes, the immunoglobulin-related genes contain separate functional regions, each having one or more distinct biological activities, the genes may be fused to functional regions from other genes to produce fusion proteins having novel properties.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection marker, e.g., tetracycline or neomycin, to permit detection of those cells transformed with the desired DNA sequences (see, e.g., U.S. Pat. No. 4,704,362, which is incorporated herein by reference).

*E. coli* is one prokaryotic host useful particularly for cloning the polynucleotides of the present invention. Other microbial hosts suitable for use include bacilli, such as *Bacillus subtilus*, and other enterobacteriacea, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, *From Genes to Clones*, VCH Publishers, N.Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc., or transformed B-cells of hybridomas. Expression vectors for these cells can include expression control sequences, such as an origin of replication, a promoter, and enhancer (Queen et al., *Immunol. Rev.* 89, 46-68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis et al., *Molecular Cloning: A Laboratory Manual*, Cold Spring Harbor Press (1982), which is incorporated herein by reference.)

Once expressed, the whole antibodies, their dimers, individual light and heavy chains, or other immunoglobulin forms of the present invention can be purified according to standard procedures in the art, including ammonium sulfate precipitation, affinity columns, column chromatography, gel electrophoresis and the like (see, generally, Scopes, R., *Protein Purification*, Springer-Verlag, N.Y. (1982), which is incorporated herein by reference). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods*, Vols. I and II, Lefkovits and Pernis, eds., Academic Press, New York, N.Y. (1979 and 1981).

The immunoglobulins of the present invention will typically find use individually in treating the toxic effects of Verotoxin Producing *E. coli* (VTEC) infection and Hemolytic Uremic Syndrome (HUS) and/or in neutralizing VT2 antigens. By way of example but not limitation, some typical disease states suitable for treatment include hemorrhagic colitis locally in the gut, renal dysfunction, and brain damage.

The humanized immunoglobulins and pharmaceutical compositions thereof of this invention are particularly useful for parenteral administration, i.e., subcutaneously, intramuscularly or intravenously. The compositions for parenteral administration will commonly comprise a solution of the immunoglobulin or a cocktail thereof dissolved in an acceptable carrier, preferably an aqueous carrier. A variety of aqueous carriers can be used, e.g., water, buffered water, 0.4% saline, 0.3% glycine, 5% glucose, human albumin solution and the like. These solutions are sterile and generally free of particulate matter. These compositions may be sterilized by conventional, well-known sterilization techniques. The compositions may contain pharmaceutically acceptable auxiliary substances as required to approximate physiological conditions such as pH adjusting and buffering agents, tonicity agents, toxicity adjusting agents and the like, for example sodium acetate, sodium chloride, potassium chloride, calcium chloride, sodium lactate, sodium citrate, etc. The concentration of immunoglobulin in these formulations can vary widely, i.e., from the less than about 0.5%, usually at least about 1% to as much a 15 or 20% by weight and will be selected primarily based on fluid volumes, viscosities, etc., in accordance with the particular mode of administration selected.

Thus, a typical pharmaceutical composition for injection could be made up to contain 1 ml sterile buffered water, and 1-10 mg of immunoglobulin. A typical composition for intravenous infusion could be made up to contain 250 ml of sterile Ringer's solution, and 150 mg of immunoglobulin. Actual methods for preparing parentally administrable compositions will be known or apparent to those skilled in the art and are described in more detail in, for example, *Remington's Pharmaceutical Science,* $15^{th}$ ed., Mack Publishing Company, Easton, Pa. (1980), which is incorporated herein by reference.

The immunoglobulins of this invention can be frozen or lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of immunoglobulin activity loss (e.g., with conventional immune globulins, IgM antibodies tend to have greater activity loss than IgG antibodies) and that use levels may have to be adjusted to compensate.

The compositions containing the present humanized immunoglobulins or a cocktail thereof can be administered for therapeutic or prophylactic treatments. In therapeutic application, compositions are administered to a patient already suffering from Verotoxin Producing *E. coli* (VTEC) infection and Hemolytic Uremic Syndrome (HUS), or other toxic manifestations from VT2 antigens, in an amount sufficient to cure or at least partially arrest the toxic syndrome and its complications. An amount adequate to accomplish this is defined as a "therapeutically effective dose." In prophylactic applications, compositions are administered to patients at risk of infection in an amount sufficient to prevent or detectably inhibit such infection and/or toxic manifestation thereof due to VT2 antigens. Amounts effective for such uses depend upon the severity of the disease and the general state of the patient's own immune system, but generally range from 0.1 to 5 mg/kg of immunoglobulin per patient dose being commonly used. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the present humanized immunoglobulins of this invention, it is possible and may be felt desirable by the treating physician to administer substantial excesses of these immunoglobulins.

Single or multiple administrations of the compositions can be carried out with dose levels and pattern being selected by the treating physician. In any event, the pharmaceutical formulations should provide a quantity of the immunoglobulin (s) of this invention sufficient to effectively treat the patient.

In particular embodiments, compositions comprising humanized immunoglobulin of the present invention may be used to detect VT2 antigens in Verotoxin Producing *E. coli* (VTEC) infection and Hemolytic Uremic Syndrome (HUS) and/or in other infections producing VT2 or VT2V. Thus, a humanized immunoglobulin of the present invention, such as a humanized immunoglobulin that binds to the antigen determinant identified by the MuVTm1.1 antibody may be labeled and used to identify anatomic sites that contain significant concentrations of VT2 or VT2V. For example but not for limitation, one or more labeling moieties may be attached to the humanized immunoglobulin. Exemplary labeling moieties include, but are not limited to, radiopaque dyes, radiocontrast agents, fluorescent molecules, spin-labeled molecules, enzymes, or other labeling moieties of diagnostic value, particularly in radiologic or magnetic resonance imaging techniques.

Humanized immunoglobulins of the present invention can further find a wide variety of utilizes in vitro. By way of example, the immunoglobulins can be utilized for detection of VT2 antigens, or the like.

For diagnostic purposes, the immunoglobulins may either be labeled or unlabeled. Unlabeled immunoglobulins can be used in combination with other labeled antibodies (second antibodies) that are reactive with the humanized immunoglobulin, such as antibodies specific for human immunoglobulin constant regions. Alternatively, the immunoglobulins can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

Kits can also be supplied for use with the subject immunoglobulins in the protection against or detection of a cellular activity or for the presence of a selected antigen. Thus, the subject immunoglobulin composition of the present invention may be provided, usually in a lyophilized form in a container, either alone or in conjunction with additional antibodies specific for the desired cell type. The immunoglobulins, which may be conjugated to a label or toxin, or unconjugated, are included in the kits with buffers, such as Tris, phosphate, carbonate, etc., stabilizers, preservatives, biocides, inert proteins, e.g., serum albumin, or the like, and a set of instructions for use. Generally, these materials will be present in less than about 5% wt. based on the amount of active immunoglobulin, and usually present in total amount of at least about 0.001% wt. based again on the immunoglobulin concentration. Frequently, it will be desirable to include an inert extender or excipient to dilute the active ingredients, where the excipient may be present in from about 1 to 99% wt. of the total composition. Where a second antibody capable of binding to the immunoglobulin is employed in an assay, this will usually be present in a separate vial. The second antibody is typically conjugated to a label and formulated in an analogous manner with the immunoglobulin formulations described above.

Human Antibodies

In another aspect of the invention, human antibodies that compete with mouse VTm1.1 for binding to verotoxin II or verotoxin II variant are provided.

a. Trioma Methodology

The basic approach and an exemplary cell fusion partner, SPAZ-4, for use in this approach have been described by Oestberg et al., *Hybridoma* 2:361-367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The B-lymphocytes are obtained from the blood, spleen, lymph nodes or bone marrow of a human donor. In vivo immunization of a living human with verotoxin II or verotoxin II variant is usually undesirable because of the risk of initiating a harmful response. Thus, B-lymphocytes are usually immunized in vitro with these antigens or an antigenic fragment of either of these, or a cell bearing either of these. B-lymphocytes are typically exposed to antigen for a period of 7-14 days in a media such as RPMI-1640 (see Engleman, supra) supplemented with 10% human serum.

The immunized B-lymphocytes are fused to a xenogeneic hybrid cell such as SPAZ-4 by well known methods. For example, the cells are treated with 40-50% polyethylene glycol of MW 1000-4000, at about 37 degrees, for about 5-10 min. Cells are separated from the fusion mixture and propagated in media selective for the desired hybrids (e.g., HAT or AH). Clones secreting antibodies having the required binding specificity are identified by assaying the trioma culture medium for the ability to bind to verotoxin II or verotoxin II variant. Triomas producing human antibodies having the desired specificity are subcloned by, e.g., the limiting dilution technique and grown in vitro in culture medium.

Although triomas are genetically stable they may not produce antibodies at very high levels. Expression levels can be increased by cloning antibody genes from the trioma into one or more expression vectors, and transforming the vector into a cell line such as the cell lines discussed, infra, for expression of recombinant or humanized immunoglobulins.

b. Transgenic Non-Human Mammals

Human antibodies reactive with verotoxin II and/or verotoxin II toxin can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); Kucherlapati, WO 91/10741 (1991) (each of which is incorporated by reference in its entirety for all purposes). Transgenic mice are particularly suitable. Antibodies are obtained by immunizing a transgenic nonhuman mammal, such as described by Lonberg or Kucherlapati, supra. Monoclonal antibodies are prepared by, e.g., fusing B-cells from such mammals to suitable myeloma cell lines using conventional Kohler-Milstein technology.

The following examples are offered by way of illustration, not by limitation. It will be understood that although the examples pertain to the HuVTm1.1 antibody, producing humanized antibodies with high binding affinity for the B subunit of the VT2 antigen it is also contemplated using CDR's from other monoclonal antibodies that bind to an epitope of VT2.

EXPERIMENTAL

Example 1

Immunization of Mice with VT2 Toxoid

VT2 was prepared as described by Oku et al., *Microb. Pathog.,* 1989, 6(2), 113-122. The VT2 toxoid was prepared by treating 1 mg of purified VT2 for 7 days at 37° C. with 0.4% formaldehyde in 0.1 M phosphate buffer, pH 7.6.

Balb/c mice (Nippon Charles River) were immunized with VT2 toxoid (0.5 µg) combined with Freund's Complete Adjuvant (Gibco BRL) by intraperitoneal (i.p.) injection. After about 4 weeks, the mice received VT2 toxoid (1 µg) combined with Freund's Complete Adjuvant by i.p. injection. Then the mice received VT2 toxoid (1 µg twice, 4 µg twice, 5 µg once) combined with Freund's Incomplete Adjuvant by i.p. injection sequentially at an interval of 1 to 5 weeks.

Mice were bled by cutting the tail vein and serum was collected by incubation of the blood for 30 min. at 37° C. and centrifugation at 3000 rpm for 10 min. The serum titer against VT2 was measured by ELISA as follows:

Each well of 96 well flat bottomed plate (Falcon 3912, Becton Dickinson) was coated with 50 µl of 1 µg/ml VT2 diluted with 0.01 M phosphate buffered saline (PBS) and incubated at r.t. for 1 hr.

Each well was washed 3 times with PBS—0.05% Tween 20.

Each well was blocked with PBS—3% BSA at r.t. for 1 hr.

Each well was washed 3 times with PBS—0.05% Tween 20.

50 µl of serum serially diluted with PBS was added to each well and incubated at r.t. for 1 hr.

Each well was washed 3 times with PBS—0.05% Tween 20.

To each well was added 50 µl of alkaline phosphatase conjugated goat anti-mouse IgG (ZYMED) diluted (×1000) with PBS—3% BSA and incubated at r.t. for 1 hr.

Each well was washed 3 times with PBS—0.05% Tween 20.

To each well was added p-nitrophenyl phosphate (PNPP: Wako Chemicals) and incubated at r.t. for 1 hr.

The absorption at 405 nm was measured and recorded for each well.

Example 2

Construction of Hybridoma by Cell Fusion Method

Mice whose serum contained antibodies reactive against VT2 were chosen and splenectomized. $5\times10^7$ spleen cells and $5\times10^6$ P3×63 Ag8U.1 (P3U1) mouse myeloma cells were combined and washed once with RPMI 1640 medium and centrifuged at 1500 rpm for 5 min. The cell pellet was gently dispersed and resuspended in 1 ml of polyethyleneglycol (PEG) solution (containing RPMI 1640 medium 5.75 ml+PEG 3.5 ml+dimethylsulfoxide 0.75 ml) and gently rotated for 2 min. Then 1 ml of RPMI medium was added and rotated for 2 min. After that, 2 ml of RPMI medium was added and rotated for 2 min. 4 ml of GIT-HAT medium (95 µM hypoxanthine, 0.4 µM aminopterin, 1.6 µM thymidine, 5% FCS) was added and rotated for 2 min. Then 8 ml of GIT-HAT medium was added and rotated for 2 min. After 30 min. incubation at 37° C. the cell suspension was delivered into each well of the 96 well flat bottomed plate inoculated with $10^4$ mouse peritoneal macrophage/well. The plate was incubated at 37° C. in 5% CO2—95% air incubator for one week. Then half of the medium in each well was replaced with fresh GIT-HT medium (GIT-HAT medium without aminoferin) and the plate was incubated for about one week to grow hybridoma cells.

Example 3

Screening of Mouse Hybridoma Cells Secreting Antibody Against VT2

Screening was done by selecting hybridoma cells secreting antibodies which bind to VT2 and neutralize VT2. Hybridoma supernatant was used for the screening. Binding activity was measured according to the ELISA method described in Example 1. VT2 neutralization activity was measured according to the following method.

To each well of a 96 well plate was added 30 µl of hybridoma supernatant and 30 µl of 200 pg/ml VT2 in 10% FCS-MEM.

The plate was incubated at 37° C. for 1 hr.

50 µl of the above solution was added to each well of a 96 well flat bottomed plate on which a Vero cell (ATCC) was inoculated ($4\times10^4$ cells/well).

The plate was incubated at 37° C. for 4 days in a 5% CO2—95% air incubator.

100 µl of a 0.014% neutral red solution was added to each well.

The plate was incubated at 37° C. for 1 hr. to stain live cells.

After washing the well with PBS, 100 µl of 50% ethanol solution containing 1% acetic acid (ETOH-AcOH) solution was added to each well.

The absorption at 550 nm was measured and recorded for each well.

Example 4

Cloning of Hybridoma Cells

Cloning of hybridoma cells was conducted by limiting dilution. One to two hybridoma cells were added to each well of a 96 well flat bottomed plate previously inoculated with $10^4$ mouse peritoneal macrophages as the feeder cells. After about 2 weeks, the supernatant was measured for the binding to VT2 and neutralization against VT2 as described in Examples 1 and 3, respectively. By repeating this cloning procedure several times as described above, a hybridoma cell clone secreting a monoclonal antibody (MuVTm1.1) which neutralizes VT2 was established. The hybridoma cell clone secreting MuVTm1.1, Accession NO. FERM BP-10877, was deposited under the Budapest Treaty at the International Patent Organism Depository, National Institute of Advanced Industrial Science and Technology, AIST Tsukuba Central 6, 1-1, Higashi 1-chome, Tsukuba-shi, Ibaraki-ken, 305-8566, Japan on Jul. 24, 2007.

Example 5

Purification of MuVTm1.1

Figure 7:
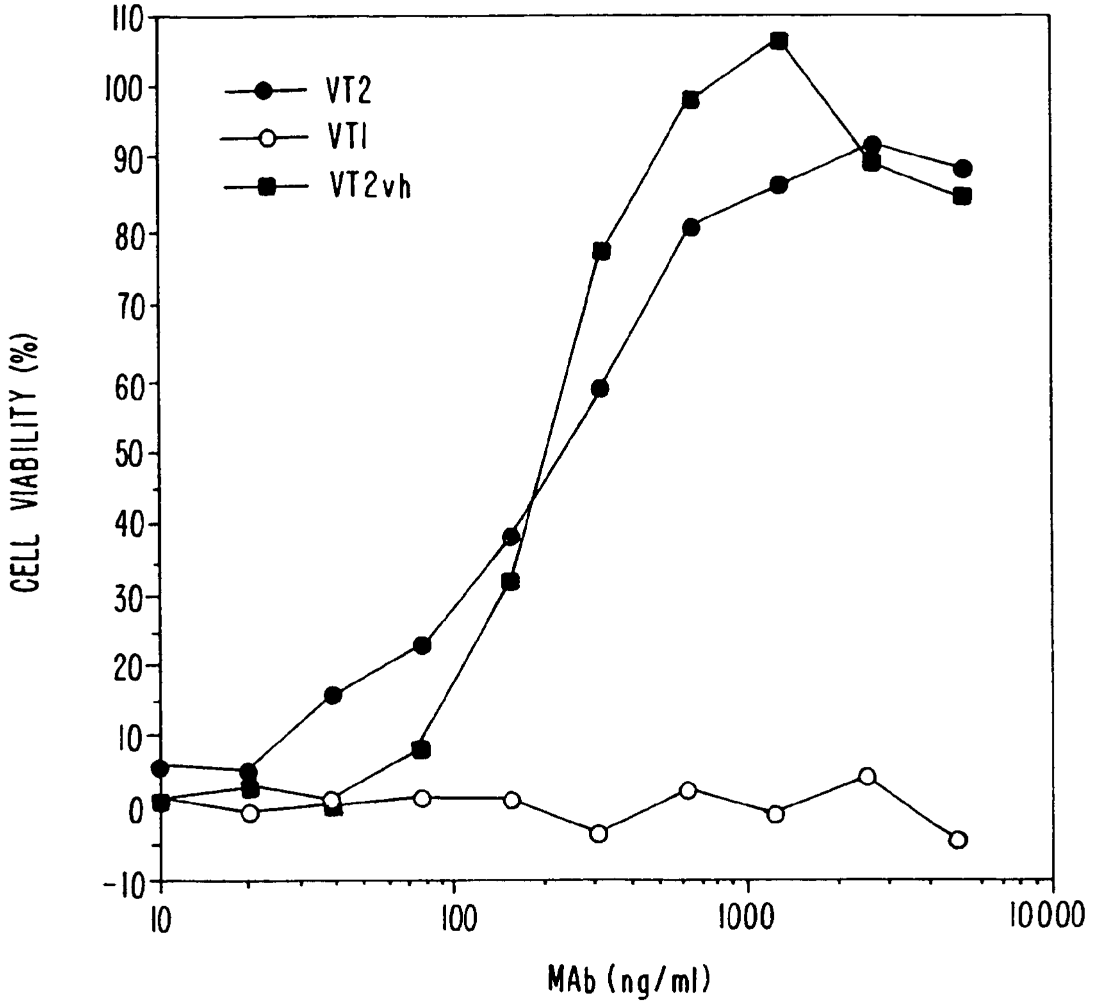
FIG. 7. Neutralizing activity of MuVTm1.1 against VT2 and VT2 variant.

The hybridoma cells secreting MuVTm1.1 were adapted to eRDF basal serum free medium containing insulin, transferrin, ethanolamine, and selenite. The culture supernatant was passed over a Protein G sepharose column (Pharmacia) and the antibody eluted using standard methods. The purity of the antibody was verified by polyacrylamide gel electrophoresis (PAGE), and its concentration was determined by SRID. The purified MuVTm1.1 was tested for its ability to neutralize VT2 variants as described in Example 3. The results are presented in the table below and in FIG. 7.

TABLE 1

Neutralizing Activity of MuVTm1.1 Against Various VT2 Variants

| Strains | Origin | Toxin Type | Neutralization |
|---|---|---|---|
| *E. coli* 0157 V50 | Human | VT2vh | + |
| *E. coli* 0157 V354 | Human | VT2vh | + |
| *E. coli* 0157 V601 | Human | ? | + |
| *E. coli* 0157:H7 TK40 | Human | VT2, VT2vx1* | + |
| *E. coli* 0157:H7 TK51 | Human | VT2vx1 | + |
| *E. coli* 091:H21 | Human | VT2vha, VT2vhb | + |

*VT2vx is a novel subtype of VT2 variant

Example 6

Cloning and Sequencing of Mouse VTm1.1 Variable Region cDNAs

Mouse VTm1.1 (MuVTm1.1) heavy and light chain variable region cDNAs were cloned from mRNA isolated from hybridoma cells using anchored PCR (Co et al., *J. Immunol.* 148: 1149 (1992)). The 5' primers used annealed to the poly-dG tails added to the cDNA, and the 3' primers to the constant regions. The amplified gene fragments were then inserted into the plasmid pUC18. Nucleotide sequences were determined from several independent clones for both $V_L$ and $V_H$ cDNA. For the heavy chain, a single, unique sequence was identified, typical of a mouse heavy chain variable region. For the light chain, two unique sequences, both homologous to mouse light chain variable region sequences, were identified. However, one sequence was not functional because of a missing nucleotide that caused a frame shift at the V-J junction, and was identified as the non-productive allele. The other sequence was typical of a functional mouse kappa chain variable region. The variable region cDNA sequences of the heavy chain and the functional light chain and the translated amino acid sequences are shown in FIG. 1. The mouse $V_E$ sequence belongs to Kabat's mouse kappa chain subgroup V. The mouse $V_H$ belongs to Kabat's heavy chain subgroup III(D).

Example 7

Design of Humanized VTm1.1 Variable Regions

To retain the binding affinity of the mouse antibody in the humanized antibody, the general procedures of Queen et al. were followed (Queen et al. *Proc. Natl. Acad. Sci. USA* 86: 10029 (1989) and U.S. Pat. Nos. 5,585,089 and 5,693,762). The choice of framework residues can be critical in retaining high binding affinity. In principle, a framework sequence from any human antibody can serve as the template for CDR grafting; however, it has been demonstrated that straight CDR replacement into such a framework can lead to significant loss of binding affinity to the antigen (Glaser et al., *J. Immunol.* 149:2606 (1992); Tempest et al., *Biotechnology* 9:266 (1992); Shalaby et al., *J. Exp. Med.* 17:217 (1992)). The more homologous a human antibody is to the original mouse antibody, the less likely will the human framework introduce distortions into the mouse CDRs that could reduce affinity. Based on a sequence homology search against the Kabat database (Kabat et al., *Sequences of Proteins of Immunological Interest,* 5th ed., U.S. Department of Health and Human Services, 1991), the human antibody GF4 was chosen as providing good framework homology to the MuVTm1.1 antibody. Other highly homologous human antibody chains would also be suitable to provide the humanized antibody framework, especially kappa light chains from human subgroup III and heavy chains from human subgroup III as defined by Kabat.

The computer programs ABMOD and ENCAD (Levitt et al., *J. Mol. Biol.* 168: 595 (1983)) were used to construct a molecular model of the VTm1.1 variable domain, which was used to locate the amino acids in the VTm1.1 framework that are close enough to the CDRs to potentially interact with them. To design the humanized VTm1.1 heavy and light chain variable regions, the CDRs from the mouse VTm1.1 antibody were grafted into the framework regions of the human GF4 antibody. At framework positions where the computer model suggested significant contact with the CDRs, the amino acids from the mouse antibody were substituted for the original human framework amino acids. For humanized VTm1.1, this was done at residues 29, 30, 49 and 98 of the heavy chain and at residue 49 of the light chain. Furthermore, framework residues that occurred only rarely at their positions in the database of human antibodies were replaced by a human consensus amino acid at those positions. For humanized VTm1.1 this was done at residues 1, 4, 5, 79, 89 and 93 of the heavy chain and at residues 3, 4, 19, 76, 79 and 85 of the light chain.

The sequence of the humanized VTm1.1 antibody heavy chain and light chain variable regions, including the initiation codon and the signal peptide sequences, are shown in FIG. 2. However, many of the potential CDR-contact residues are amenable to substitutions of other amino acids that may still allow the antibody to retain substantial affinity to the antigen. The following table lists a number of positions in the framework where alternative amino acids may be suitable (LC=light chain, HC=heavy chain).

TABLE 2

| Position | Humanized VTm1.1 | Alternatives |
|---|---|---|
| LC-49 | K | Y |
| HC-29 | F | S |
| HC-30 | S | K |
| HC-49 | A | S |
| HC-98 | R | K |

Likewise, many of the framework residues not in contact with the CDRs in the humanized VTm1.1 heavy and light chains can accommodate substitutions of amino acids from the corresponding positions of the human GF4 antibody, from other human antibodies, from the mouse VTm1.1 antibody, or from other mouse antibodies, without significant loss of the affinity or non-immunogenicity of the humanized antibody. The following table lists a number of additional positions in the framework where alternative amino acids may be suitable.

TABLE 3

| Position | Humanized VTm1.1 | Alternatives |
|---|---|---|
| LC-3 | V | L |
| LC-4 | L | M |
| LC-19 | A | V |
| LC-76 | S | N |
| LC-79 | E | Q |
| LC-85 | V | L, M |
| HC-1 | E | Q |
| HC-4 | L | V |
| HC-5 | V | L |
| HC-79 | L | V |
| HC-89 | E | D |
| HC-93 | V | M, I |

Selection of various alternative amino acids may be used to produce versions of humanized VTm1.1 that have varying combinations of affinity, specificity, non-immunogenicity, ease of manufacture, and other desirable properties. Thus, the examples in the above tables are offered by way of illustration, not of limitation.

Example 8

Construction of Humanized VTm1.1

Once the humanized variable region amino acid sequences had been designed as described above, genes were constructed to encode them, including signal peptides, splice donor signals and appropriate restriction sites (FIG. 2). The light and heavy chain variable region genes were constructed and amplified using eight overlapping synthetic oligonucleotides ranging in length from approximately 65 to 80 bases, as shown in FIG. 3 (see He et al. *J. Immunol.* 160: 1029 (1998)). The oligos were annealed pairwise and extended with the Klenow fragment of DNA polymerase I, yielding four double-stranded fragments. The resulting fragments were denatured, annealed, and extended with Klenow, yielding two fragments. These fragments were denatured, annealed pairwise, and extended once again, yielding a full-length gene. The resulting product was amplified by polymerase chain reaction (PCR) using Tag polymerase, gel-purified, digested with XbaI, gel-purified again, and subcloned into the XbaI site of the pVk or pVgl expression vector. The pVk and pVgl vectors for the respective light chain and heavy chain expression have been previously described (see Co et al., *J. Immunol.* 148:1149 (1992)).

The structure of the final plasmids were verified by nucleotide sequencing and restriction mapping. All DNA manipulations were performed by standard methods well-known to those skilled in the art.

To construct a cell line producing humanized VTm1.1, the heavy chain and light chain plasmids were transfected into the mouse myeloma cell line Sp2/0-Ag14 (ATCC CRL 1581). Before transfection, the heavy and light chain-containing plasmids were linearized using FspI. Approximately 20 μg of each plasmid was transfected into $1\times10^7$ cells in PBS. Transfection was by electroporation using a Gene Pulser apparatus (BioRad) at 360 V and 25 μFD capacitance according to the manufacturer's instructions. The cells from each transfection were plated in four 96-well tissue culture plates, and after two days, selection medium (DMEM, 10% FCS, 1×HT supplement (Sigma), 0.25 mg/ml xanthine, 1 μg/ml mycophenolic acid) was applied.

After approximately two weeks, the clones that appeared were screened for antibody production by ELISA. Antibody from a high-producing clone was prepared by growing the cells to confluency in regular medium (DMEM with 10% FCS), then replacing the medium with a serum-free medium (Hybridoma SMF; Gibco) and culturing until maximum antibody titers were achieved in the culture. The culture supernatant was run through a protein A-Sepharose column (Pharmacia); antibody was eluted with 0.1 M Glycine, 100 mM NaCl, pH 3, neutralized and subsequently exchanged into phosphate-buffered saline (PBS). The purity of the antibody was verified by analyzing it on an acrylamide gel, and its concentration was determined by an $OD_{280}$ reading, assuming 1.0 mg of antibody protein has an $OD_{280}$ reading of 1.4.

Example 9

Properties of Humanized VTm1.1

Affinity Measurement

The affinity of MuVTm1.1 and HuVTm1.1 antibody for verotoxin II (VT2) was determined by competitive binding with biotinylated MuVTm1.1 antibody. The procedure for the experiment is described below:

- Coated Dynatech Laboratories Immulon 2 96-well plate (part #0110103455) with 50 μl VT2 solution (0.2 μg/ml in PBS) per well. Incubated at 37° C. for 2 hr with gentle shaking.
- Aspirated off the VT2 solution. Washed each well 4 times with 400 μl of wash buffer (0.1% Tween 20 in PBS).
- Blocked each well with 400 μl of Pierce SuperBlock Blocking Buffer in PBS (cat #37515) at room temperature for 30 min.
- Aspirated off the blocking solution. Washed each well 4 times with 400 μl of wash buffer.
- In each well added 20 ng biotinylated MuVTm1.1 antibody mixed with various concentrations of unlabeled mouse or Hu VTm1.1 antibodies in a total volume of 100 μl in binding buffer (1% BSA, 0.1% Tween 20 in PBS). Incubated at 4° C. overnight with gentle shaking. Aspirated off the antibody solutions. Washed each well 4 times with 400 μl of wash buffer.
- Added 100 μl of peroxidase-conjugated strepavidin (Bioscource cat #5NN2004) (1:500 dilution in binding buffer) to each well. Incubated at 37° C. for 1 hr with gentle shaking.
- Aspirated off the strepavidin solution. Washed each well 6 times with 400 μl of wash buffer.

Added 100 μl/well peroxidase substrate (BioRad #172-1064). Incubated at room temperature until the color developed. Read the plate in Molecular Devices ELISA plate reader at 415 nm.

Figure 4:
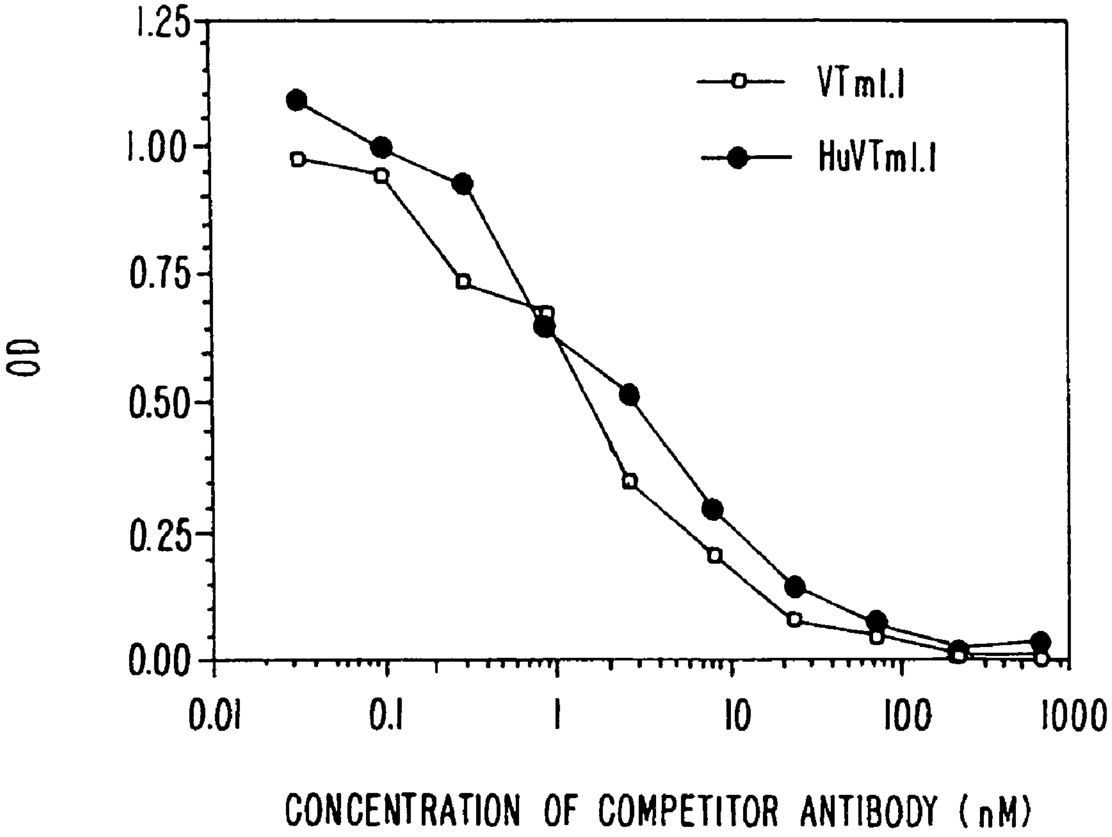
FIG. 4. Competitive binding of MuVTm1.1 and HuVTm1.1 antibodies to *E. coli* Verotoxin II (VT2). Increasing concentrations of competitor antibody were incubated with coated VT2 in the presence of biotinylated tracer MuVTm1.1. Absorbance was measured and plotted against the concentration of the unlabeled competitor antibodies.

The result, shown in FIG. 4, demonstrated that the humanized VTm1.1 antibody competes well against the biotinylated mouse antibody in the competitive ELISA assay, within a factor of 2 when compared to the mouse antibody.

The affinity of HuVTm1.1 and MuVTm1.1 is also calculated using the BIAcore method. The calculated $K_D$ for the HuVTm1.1 is approximately $3.6\times10^{-9}$ M versus $1.9\times10^{-9}$ M for the Mu VTm1.1 as shown in the Table below:

TABLE 4

| | MuVTm1.1 | HuVTm1.1 |
|---|---|---|
| $K_a$ | $9.9\times10^4\ M^{-1}\ S^{-1}$ | $9.5\times10^4\ M^{-1}\ S^{-1}$ |
| $K_d$ | $1.9\times10^{-4}\ S^{-1}$ | $3.4\times10^{-4}\ S^{-1}$ |
| $K_D$ | $1.9\times10^{-9}$ M | $3.6\times10^{-9}$ M |

Example 10

In Vitro Neutralizing Activity of HuVTm1.1

The neutralizing activity of HuVTm1.1 is also measured compared to mouse MuVTm1.1 in an in vitro assay described below:

Human kidney derived cell line (ACHN) was inoculated onto a 96-well plate at $1\times10^4$ cells/well and incubated at 37° C. for 24 hr.

Medium was aspirated and 50 μl of a mixed solution of 30 μl of 540 pg/ml VT2 solution diluted with 10% FCS-MEM and 30 μl of test antibody serially diluted with 10% FCS-MEM (mouse or humanized VTm1.1) preincubated at 37° C. for 1 hr was added onto each well and incubated at 37° C. for four days.

100 μl of 0.028% neutral red in medium was added to each well and incubated at 37° C. for 1 hr (Mullbacher, A. et al., 1984, Journal of Immunological Methods, 68, 205-215).

Solution was aspirated. Each well was washed twice with 150 μl of PBS.

100 μl of 50% EtOH/1% AcOH was added to each well and incubated at room temperature for 5-10 min.

The absorption value at 550 nm was recorded for each well using a Molecular Devices ELISA plate reader.

Neutralizing activity was calculated according to the following formula:

$$\text{Neutralization (\%)} = \frac{OD\ (VT2 + Ab) - OD\ (VT2\ \text{alone})}{OD\ (\text{medium alone}) - OD\ (VT2\ \text{alone})} \times 100$$

Figure 5:
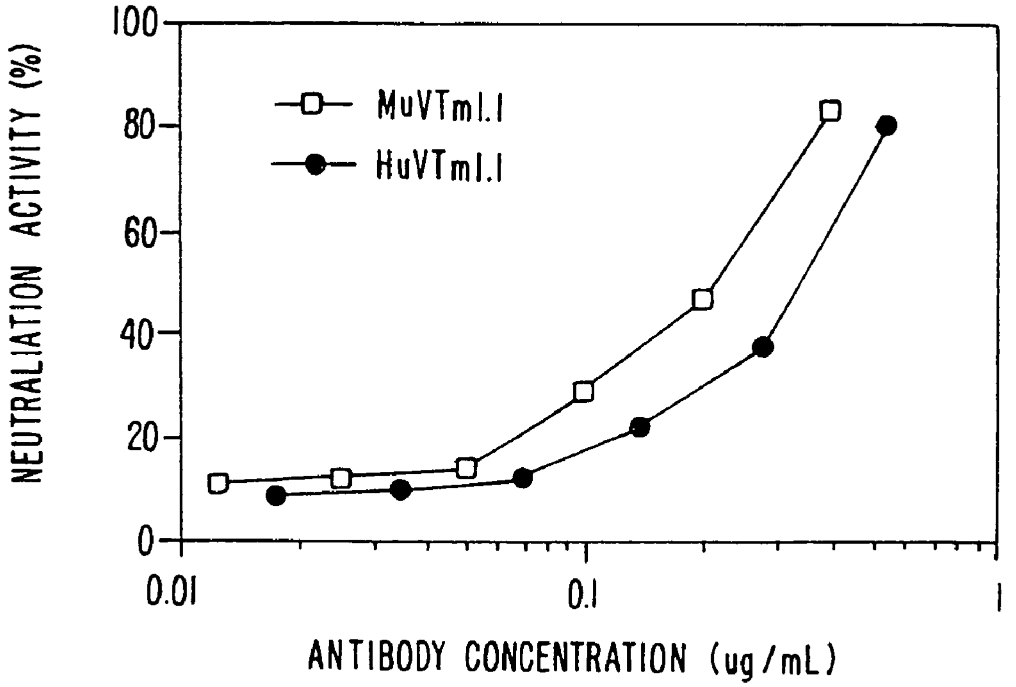
FIG. 5. In vitro neutralizing activity of HuVTm1.1 versus MuVTm1.1.

The neutralizing activity of HuVTm1.1 compared to MuVTm1.1 is shown in FIG. 5. The ED50 for the HuVTm1.1 is 0.33 μg/ml versus 0.2 μg/ml for MuVTm1.1. The neutralization activity of HuVTm1.1 to VT2 variants is shown below:

TABLE 5

| In vitro VT2variants neutralizing assay with HuVTm1.1 | | | |
|---|---|---|---|
| Strains | Origin | Toxin Type | ED50 (μg/ml) |
| *E. coli* 0157 | Human | VT2 | 0.33 |
| *E. coli* 0157 (V50) | Human | VT2vh | 0.36 |
| *E. coli* 0157 (V354) | Human | VT2vh | 0.39 |
| *E. coli* 0157 (V601) | Human | VT2v | 0.32 |
| *E. coli* 0157:H7 (TK 40) | Human | VT2, VT2vx* | 0.35 |

*VT2vx: Novel subtype of VT2 variant

Example 11

Analysis of VT2 Antigen Recognized

Figure 6:
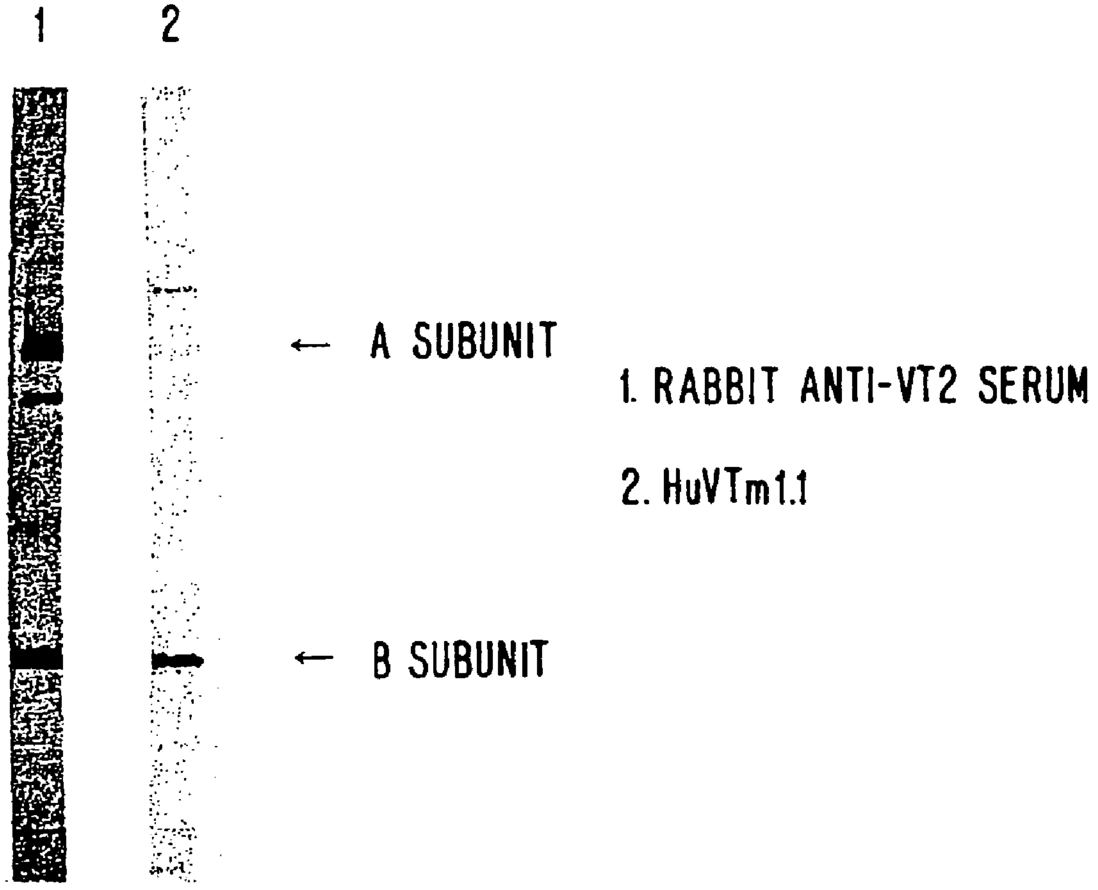
FIG. 6. Identification of recognized antigen (the B subunit of VT2) of HuVTm1.1.

VT2 was reduced, the A and B subunits were separated by polyacrylamide gel containing SDS and transferred to a nitrocellulose membrane (Bio Rad) by Western Blotting method. The nitrocellulose membrane was blocked overnight in 3% BSA in PBS and then reacted with 10 μg/ml of HuVTm1.1 or rabbit anti-VT2 serum diluted with 3% BSA in PBS for 1 hr. at r.t. The membrane was washed 6 times with 1% BSA-PBS and reacted with 25 μg/ml alkaline phosphatase conjugated goat anti-human IgG (TAGO) or alkaline phosphatase conjugated goat anti-rabbit IgG (TAGO) diluted with 3% BSA in PBS for 1 hr. at r.t. The membrane was washed 6 times with 1% BSA in PBS and reacted with NBT (Nitro-Blue Tetrazolium Chloride)—BCIP (5-Bromo-4-Chloro-3'-Indolyephosphate p-Toluidine salt) solution [PIERCE] for 10 min. at r.t. The result shown in FIG. 6 indicates that HuVTm1.1 principally binds to the B subunit of VT2.

Example 12

In Vivo Activity of HuVTm1.1 Against VT2

DdY mice (Nippon SLC) were injected via the intravenous route with 4.8 μg of sterilized HuVTm1.1, MuVTm1.1 or PBS. One hour later, mice were injected via the intraperitoneal (i.p.) route with 46 ng of VT2 (corresponding to 10 $LD_{50}$). After a week, viability of mice was measured.

The following table shows the result. HuVTm1.1 completely protects mice from death caused by VT2.

TABLE 6

| TREATMENT | SURVIVORS |
|---|---|
| PBS | 100% (5/5) |
| VT2 | 0% (0/5) |
| HuVTm1.1 + VT2 | 100% (5/5) |
| MuVTm1.1 + VT2 | 100% (5/5) |

From the foregoing, it will be appreciated that the humanized immunoglobulins of the present invention offer numerous advantages over other anti VT specific antibodies. In comparison to mouse monoclonal antibodies, the present humanized immunoglobulins contain substantially less non-human and potentially immunogenic amino acid sequences. This reduced likelihood of antigenicity after injection into a human patient represents a significant therapeutic improvement.

All publications and patent applications cited above are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

We claim:

1. A humanized antibody that is a humanized form of a mouse antibody characterized by a light chain variable region of SEQ ID NO:4 and a heavy chain variable region of SEQ ID NO:2, wherein the humanized antibody binds to verotoxin II (VT2).

2. A humanized antibody that competes with the mouse antibody deposited as Accession No. FERM BP-10877 for binding to VT2.

3. A humanized antibody of claim 1 comprising complementarity determining regions from the mouse antibody and heavy and light chain variable region frameworks from the human GF4 antibody heavy (SEQ ID NO: 9) and light (SEQ ID NO:10) chains, provided that at least one position selected from the group consisting of L49, H29, H30, H49 and H98, is occupied by the amino acid present in the equivalent position of the mouse antibody heavy or light chain variable region framework, which humanized antibody binds to verotoxin II.

4. The humanized antibody of claim 3, provided that each position selected from the group consisting of L49, H29, H30, H49 and H98 is occupied by the amino acid present in the equivalent position of the mouse antibody heavy or light chain variable region framework.

5. The humanized antibody of claim 4, provided that at least one position selected from the group L3, L4, L19, L76, L79, L85, H1, H4, H5, H79, H89 and H93 is occupied by an amino acid present in the equivalent position of a human antibody heavy or light chain consensus sequence.

6. The humanized antibody of claim 5, provided that each position selected from the group L3, L4, L19, L76, L79, L85, H1, H4, H5, H79, H89 and H93 is occupied by an amino acid present in the equivalent position of a human antibody heavy or light chain consensus sequence.

7. The humanized antibody of claim 1 comprising a heavy chain variable region of SEQ ID NO:6 and a light chain variable region of SEQ ID NO:8 provided that one or more positions may be substituted as follows: L49 from K to Y, H29 from F to S, H30 from S to K, H49 from A to R, H98 from R to K, L3 from V to L, L4 from L to M, L19 from A to V, L76 from S to N, L79 from E to Q, L85 from V to L or M, H1 from E to Q, H4 from L to V, H5 from V to L, H79 from L to V, H89 from E to D and H93 from V to M or I.

8. The humanized antibody of claim 1 comprising a heavy chain variable region of SEQ ID NO:6 and a light chain variable region of SEQ ID NO:8.

9. The humanized antibody of claim 1, comprising a humanized heavy chain having at least 85% identity with the humanized heavy chain of SEQ ID NO:6 and a humanized light chain having at least 85% sequence identity with the humanized light chain of SEQ ID NO:8, provided that at least one position selected from the group consisting of L49, H29, H30, H49 and H98, is occupied by the amino acid present in the equivalent position of the mouse antibody heavy or light chain variable region framework.

10. The humanized antibody of claim 1 or 2, wherein the antibody comprises two pairs of light/heavy chain dimers, wherein each chain comprises a variable region and a constant region.

11. The humanized antibody of claim 1 or 2, which is a Fab fragment or a $F(ab')_2$.

12. The humanized antibody of claim 1 or 2 in purified form.

13. The humanized antibody of claim 1 or 2, which has an $IgG_1$ immunoglobulin isotype.

14. A method of producing a humanized antibody, comprising culturing a cell line, which encodes heavy and light chain chains of the humanized antibody of claim 1 or 2, whereby the humanized antibody is expressed; and recovering the humanized antibody expressed by the cell line.

15. The method of claim 14, further comprising mixing the antibody with a pharmaceutically acceptable carrier to produce a pharmaceutical composition.

16. A pharmaceutical composition comprising the humanized antibody of claim 1 or 2 and a pharmaceutically acceptable carrier.

17. A pharmaceutical composition comprising the humanized antibody of claim 8 and a pharmaceutically acceptable carrier.

18. A method of treating a patient suffering or at risk of toxic effects from a verotoxin, comprising administering to the patient an effective dosage of a human or humanized antibody that binds to verotoxin II, wherein the humanized antibody is as defined in claim 1 or claim 2.

19. The method of claim 18, wherein the antibody competes with a mouse antibody characterized by a light chain variable region of SEQ ID NO:4 and a heavy chain variable region of SEQ ID NO:2 for binding to VT2.

20. The method of claim 18, wherein the humanized antibody binds to the B subunit of VT2.

21. The method of claim 18, wherein the antibody is a humanized antibody comprising a heavy chain variable region of SEQ ID NO:6 and a light chain variable region of SEQ ID NO:8.

22. The method of claim 18, wherein the patient is infected with verotoxin producing *E. coli* and the antibody is administered therapeutically.

23. The method of claim 18, wherein the patient is at risk of infection by verotoxin producing *E. coli* and the antibody is administered prophylactically.

24. The method of claim 22, further comprising monitoring the patient for recovery from the toxic effects of VT2.

25. A cell line that produces the antibody of claim 1 or 2.

26. The humanized antibody of claim 2 that is a humanized form of a mouse immunoglobulin.

27. The humanized antibody of claim 2 that binds the same epitope as the mouse antibody deposited as Accession No. FERM BP-10877.

* * * * *